(12) United States Patent
Svendsen

(10) Patent No.: US 6,838,257 B2
(45) Date of Patent: Jan. 4, 2005

(54) PULLULANASE VARIANTS AND METHODS FOR PREPARING SUCH VARIANTS WITH PREDETERMINED PROPERTIES

(75) Inventor: Allan Svendsen, Birkerod (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/996,024

(22) Filed: Nov. 16, 2001

(65) Prior Publication Data

US 2004/0082028 A1 Apr. 29, 2004

Related U.S. Application Data

(62) Division of application No. 09/514,599, filed on Feb. 28, 2000, now Pat. No. 6,350,599.

(30) Foreign Application Priority Data

Jan. 12, 2000 (DK) ........................................ 2000 00045

(51) Int. Cl.[7] .......................... C12N 15/00; C12N 9/00; C07H 21/04; G01N 31/00

(52) U.S. Cl. ..................... 435/69.1; 435/183; 536/23.1; 702/27

(58) Field of Search ................................ 435/69.1, 183, 435/6; 536/23.1; 702/27; 530/300

(56) References Cited

U.S. PATENT DOCUMENTS 6,265,197 B1 * 7/2001 Bisg.ang.rd-Frantzen et al. ............ 435/210

* cited by examiner

Primary Examiner—Kenneth R. Horlick
Assistant Examiner—Young J. Kim
(74) Attorney, Agent, or Firm—Elias Lambiris; Jason Garbell

(57) ABSTRACT

The present invention relates to pullulanase variants, wherein the variants have improved properties, for example, altered pH optimum, improved thermostability, altered substrate specificity, increased specific activity or altered cleavage pattern. The present invention also relates to methods of making pullulanase variants having at least one altered property based on the three-dimensional structure of a parent pullulanase.

27 Claims, 1 Drawing Sheet

PULLULANASE VARIANTS AND METHODS FOR PREPARING SUCH VARIANTS WITH PREDETERMINED PROPERTIES

CROSS-REFERENCE TO RELATED APPLICATIONS

This application is a division of U.S. application Ser. No. 09/514,599 filed Feb. 28, 2000 now U.S. Pat. No. 6,350,599 and claims, under 35 U.S.C. 119, priority of Danish application no. PA 2000 00045 filed Jan. 12, 2000, the contents of which are fully incorporated herein by reference.

FIELD OF THE INVENTION

The present invention relates to variants of pullulanases and to methods for constructing such variants.

BACKGROUND OF THE INVENTION

Starches such as corn, potato, wheat, manioc and rice starch are used as the starting material in commercial large scale production of sugars, such as high fructose syrup, high maltose syrup, maltodextrins, amylose, G4–G6 oligosaccharides and other carbohydrate products such as fat replacers.

Degradation of Starch

Starch usually consists of about 80% amylopectin and 20% amylose. Amylopectin is a branched polysaccharide in which linear chains Δ-1,4 D-glucose residues are joined by Δ-1,6 glucosidic linkages. Amylopectin is partially degraded by Δ-amylase, which hydrolyzes the 1,4-Δ-glucosidic linkages to produce branched and linear oligosaccharides. Prolonged degradation of amylopectin by Δ-amylase results in the formation of so-called Δ-limit dextrins which are not susceptible to further hydrolysis by the Δ-amylase. Branched oligosaccharides can be hydrolyzed into linear oligosaccharides by a debranching enzyme. The remaining branched oligosaccharides can be depolymerized to D-glucose by glucoamylase, which hydrolyzes linear oligosaccharides into D-glucose.

Amylose is a linear polysaccharide built up of D-glucopyranose units linked together by α-1,4 glucosidic linkages. Amylose is degraded into shorter linear oligosaccharides by α-amylase, the linear oligosaccharides being depolymerized into D-glucose by glucoamylase.

In the case of converting starch into a sugar, the starch is depolymerized. The depolymerization process consists of a pretreatment step and two or three consecutive process steps, namely a liquefaction process, a saccharification process and, depending on the desired end product, optionally an isomerization process.

Pre-treatment of Native Starch

Native starch consists of microscopic granules which are insoluble in water at room temperature. When an aqueous starch slurry is heated, the granules swell and eventually burst, dispersing the starch molecules into the solution. During this "gelatinization" process there is a dramatic increase in viscosity. As the solids level is 30–40% in a typical industrial process, the starch has to be thinned or "liquefied" so that it can be handled. This reduction in viscosity is today mostly obtained by enzymatic degradation.

Liquefaction

During the liquefaction step, the long-chained starch is degraded into smaller branched and linear units (maltodextrins) by an α-amylase (e.g. Termamyl™, available from Novo Nordisk N/S, Denmark). The liquefaction process is typically carried out at about 105–110° C. for about 5 to 10 minutes followed by about 1–2 hours at about 95° C. The pH generally lies between about 5.5 and 6.2. In order to ensure an optimal enzyme stability under these conditions, calcium is added, e.g. 1 mM of calcium (40 ppm free calcium ions). After this treatment the liquefied starch will have a "dextrose equivalent" (DE) of 10–15.

Saccharification

After the liquefaction process the maltodextrins are converted into dextrose by addition of a glucoamylase (e.g. AMG™, available from Novo Nordisk A/S) and a debranching enzyme, such as an isoamylase (see e.g. U.S. Pat. No. 4,335,208) or a pullulanase (e.g. Promozyme®, available from Novo Nordisk A/S; see U.S. Pat. No. 4,560,651). Before this step the pH is reduced to a value below 4.5, e.g. about 3.8, maintaining the high temperature (above 95° C.) for a period of e.g. about 30 min. to inactivate the liquefying α-amylase to reduce the formation of short oligosaccharides called "panose precursors" which cannot be hydrolyzed properly by the debranching enzyme.

The temperature is then lowered to 60° C., glucoamylase and debranching enzyme are added, and the saccharification process proceeds for about 24–72 hours.

Normally, when denaturing the α-amylase after the liquefaction step, a small amount of the product comprises panose precursurs which cannot be degraded by pullulanases or AMG. If active amylase from the liquefaction step is present during saccharification (i.e. no denaturing), this level can be as high as 1–2% or even higher, which is highly undesirable as it lowers the saccharification yield significantly. For this reason, it is also preferred that the α-amylase is one which is capable of degrading the starch molecules into long, branched oligosaccharides (such as, e.g., the Fungamyl™-like α-amylases) rather than shorter branched oligosaccharides.

Isomerization

When the desired final sugar product is e.g. high fructose syrup, the dextrose syrup may be converted into fructose by enzymatic isomerization. After the saccharification process the pH is increased to a value in the range of 6–8, preferably about pH 7.5, and the calcium is removed by ion exchange. The dextrose syrup is then converted into high fructose syrup using, e.g., an immobilized glucose isomerase (such as Sweetzyme™, available from Novo Nordisk A/S).

Debranching Enzymes

Debranching enzymes which can attack amylopectin are divided into two classes: isoamylases (E.C. 3.2.1.68) and pullulanases (E.C. 3.2.1.41), respectively. Isoamylase hydrolyses α-1,6-D-glucosidic branch linkages in amylopectin and β-limit dextrins and can be distinguished from pullulanases by the inability of isoamylase to attack pullulan, and by their limited action on α-limit dextrins.

When an acidic stabilized α-amylase is used for the purpose of maintaining the amylase activity during the entire saccharification process (no inactivation), the degradation specificity should be taken into consideration. It is desirable in this regard to maintain the α-amylase activity throughout the saccharification process, since this allows a reduction in the amyloglucidase addition, which is economically beneficial and reduces the AMG™ condensation product isomaltose, thereby increasing the DE (dextrose equivalent) yield.

It will be apparent from the above discussion that the known starch conversion processes are performed in a series of steps, due to the different requirements of the various enzymes in terms of e.g. temperature and pH. It would therefore be desirable to be able to engineer one or more of these enzymes, e.g. pullulanases, so that the overall process could be performed in a more economical and efficient manner. One possibility in this regard is to engineer the otherwise thermolabile pullulanases so as to render them more stable at higher temperatures.

BRIEF DISCLOSURE OF THE INVENTION

The inventors have modified the amino acid sequence of a pullulanase to obtain variants with improved properties, based on the three-dimensional structure of the pullulanase Promozyme® (available from Novo Nordisk A/S). The variants have altered physicochemical properties, e.g. an altered pH optimum, improved thermostability, increased specific activity or an altered cleavage pattern.

Accordingly, the object of the present invention is to provide a method for constructing pullulanases having altered properties, in particular to provide a method for constructing pullulanases having improved thermostability, altered pH dependent activity and/or altered substrate specificity, such as increased isoamylase activity.

Thus, in its broadest aspect, the present invention relates to a method for constructing a variant of a parent pullulanase, wherein the variant has at least one altered property as compared to said parent pullulanase, which method comprises:

i) analyzing the structure of the pullulanase to identify, on the basis of an evaluation of structural considerations, at least one amino acid residue or at least one structural region of the pullulanase, which is of relevance for altering said property;

ii) constructing a variant of the pullulanase, which as compared to the parent pullulanase, has been modified in the amino acid residue or structural part identified in i) so as to alter said property; and iii) testing the resulting pullulanase variant for said property.

The property which may be altered by the above methods of the present invention may be, e.g., thermostability, pH dependent activity, specific activity, or substrate specificity. Thus, the variant may have, e.g., increased thermostability, higher activity at a lower pH, an altered pH optimum, improved thermostability, or increased specific activity, such as increased isoamylase activity.

Although it has been described in the following that modification of the parent pullulanase in certain regions and/or positions is expected to confer a particular effect to the thus produced pullulanase variant (such as an improved thermostability or an increased isoamylase activity), it should be noted that modification of the parent pullulanase in any of such regions may also give rise to any other of the above-mentioned effects. For example, any of the regions and/or positions mentioned as being of particular interest with respect to, e.g., improved thermostability, may also give rise to, e.g., higher activity at a lower pH, an altered pH optimum, or increased specific activity, such as increased isoamylase activity.

Further aspects of the present invention relates to variants of a pullulanase, the DNA encoding such variants and methods of preparing the variants. Still further aspects of the present invention relates to the use of the variants for various industrial purposes, in particular for processes where sweeteners are made from starch. Other aspects of the present invention will be apparent from the below description as well as from the appended claims.

DETAILED DISCLOSURE OF THE INVENTION

Pullulanases

Figure 1:
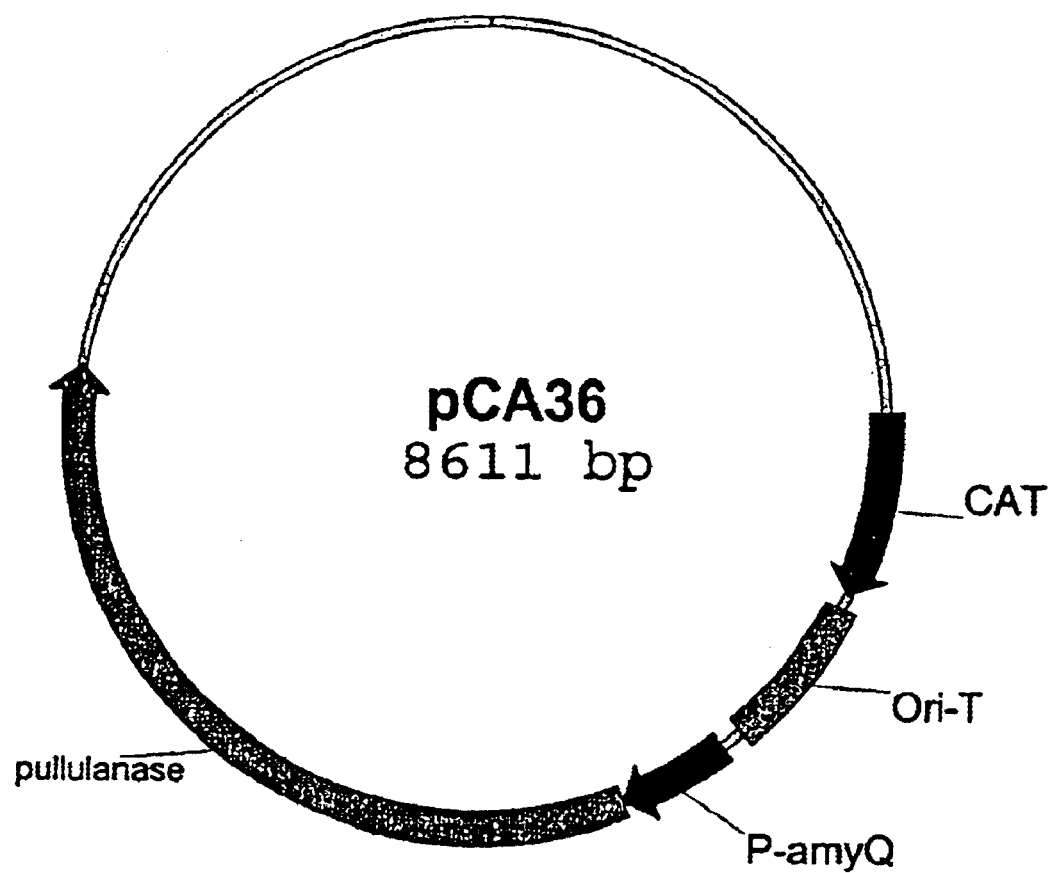
FIG. 1 shows the DNA plasmid pCA36 harboring the gene encoding the pullulanase from *Bacillus deramificans* (SEQ ID NO: 3).

As explained above, pullulanases are enzymes classified in EC 3.2.1.41 and such enzymes are characterized by their ability to hydrolyze the α-1,6-glycosidic bonds in, for example, amylopectin and pullulan.

A particularly interesting pullulanase is the pullulanase from *Bacillus acidopullulyticus* described in U.S. Pat. No. 4,560,651 (hereinafter referred to as Promozyme®). Promozyme® has the amino acid sequence set forth in amino acids 1–921 of SEQ ID NO: 1. The three-dimensional structure of Promozyme® is described below.

Another interesting pullulanase is the pullulanase from *Bacillus deramificans* described in U.S. Pat. No. 5,736,375. This enzyme has the amino acid sequence set forth in amino acid sequence 1–928 of SEQ ID NO: 3. Homology building of the tree-dimensional structure of the above-mentioned pullulanase is described below.

In general, a preferred pullulanase suitable for the purpose described herein should have one or more of the following properties:

i) A three-dimensional structure homologous to Promozyme®.

ii) An amino acid sequence which is at least 40% homologous to SEQ ID NO:1 or SEQ ID NO:3, preferably at least 50%, e.g. at least 60%, such as a least 70%, at least 75%, at least 80%, at least 85%, at least 90%, at least 91%, at least 92%, at least 93%, at least 94%, at least 95%, at least 96%, at least 97%, at least 98%, or at least 99% homologous to SEQ ID NO:1 or SEQ ID NO:3.

iii) A nucleic acid sequence which hybridizes to the nucleic acid sequence set forth in SEQ ID NO:1 or SEQ ID NO:3.

The structural homology referred to above in i) above is based on other sequence homologies, hydrophobic cluster analysis or by reverse threading (Huber, T; Torda, AE, PROTEIN SCIENCE Vol 7, No. 1 pp. 142–149 (1998)) and which by any of these methods is predicted to have the same tertiary structure as Promozyme, wherein the tertiary structure refers to the overall folding or the folding of Domains N1, N2, A, B, and C. Alternatively, a structural alignment between Promozyme and homologous sequences may be used to identify equivalent positions.

For example, the homology between various pullulanase with known amino acid sequence has been compiled in the below matrix:

|              | 1   | 2   | 3   | 4  | 5  | 6  | 7  | 8  | 9  | 10 |
|--------------|-----|-----|-----|----|----|----|----|----|----|----|
| 1. pula_kleae | 100 | 86  | 59  | 51 | 52 | 53 | 52 | 52 | 55 | 50 |
| 2. pula_klepn |     | 100 | 58  | 51 | 51 | 53 | 53 | 53 | 53 | 52 |
| 3. w81973     |     |     | 100 | 55 | 56 | 52 | 55 | 54 | 51 | 56 |

-continued

|  | 1 | 2 | 3 | 4 | 5 | 6 | 7 | 8 | 9 | 10 |
|---|---|---|---|---|---|---|---|---|---|---|
| 4. r56989 |  |  |  | 100 | 98 | 60 | 76 | 54 | 56 | 76 |
| 5. sp929mat |  |  |  |  | 100 | 61 | 78 | 54 | 57 | 78 |
| 6. fervido_x |  |  |  |  |  | 100 | 61 | 57 | 54 | 62 |
| 7. sp734 |  |  |  |  |  |  | 100 | 56 | 54 | 91 |
| 8. r71616 |  |  |  |  |  |  |  | 100 | 54 | 56 |
| 9. w09257 |  |  |  |  |  |  |  |  | 100 | 54 |
| 10. Promozyme ® |  |  |  |  |  |  |  |  |  | 100 |

| | |
|---|---|
| 1. Pula_kleae: | Pullulanase from *Klebsiella aerogenes* (J. Bacteriol. (1987) 169, 2301–2306). |
| 2. Pula_klepn: | Pullulanase from *Klebsiella pneumonia* (Mol. Microbiol. (1990) 4, 73–85; J. Bacteriol. (1985) 164, 639–645; J Bacteriol. (1989) 171, 3673–3679). |
| 3. W81973: | Pullulanase fragment from zea mays (WO 98/50562). |
| 4. r56989: | Mature pullulanase from *Bacillus deramificans* T 89.117D (EP 0 605 040). |
| 5. sp929mat: | Mature part of pullulanase from *Bacillus deramificans* (U.S. Pat. No. 5,736,375). |
| 6. fervido_x: | Mature part of pullulanase from *Fervidobacterium pennavorans* Ven5 (Appl. Environ. Microb. (1997) 63, 1088–1094). |
| 7. sp734: | Mature pullulanase from *Bacillus acidopullulyticus* (FEMS Mic. Let. (1994) 115, 97–106. |
| 8. r71616: | Pullulanase from Thermus sp. (JP 07023783). |
| 9. w09257: | Pullulanase from Bacillus sp. KSM-AP 1378 (WO 96/35794). |

The above homology calculations were determined by use of the GAP program from the UWGCG package using default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711).

A sequence alignment between Promozyme® (SEQ ID NO: 1), the pullulanase from *Bacillus deramifcans* (SEQ ID NO: 3) and the pullulanase from *Bacillus acidopullulyticus* (SEQ ID NO: 5) described in FEMS Mic. Let. (1994) 115, 97–106, is shown in Appendix 2.

Three-dimensional Structure of Pullulanase

Promozyme® was used to elucidate the three-dimensional structure forming the basis for the present invention.

The structure of Promozyme® was solved in accordance with the principle for x-ray crystallographic methods, for example, as given in *X-Ray Structure Determination*, Stout, G. K. and Jensen, L. H., John Wiley & Sons, Inc. NY, 1989.

The structural coordinates for the solved crystal structure of Promozyme® using the isomorphous replacement method are given in standard PDB format. (Protein Data Bank, Brookhaven National Laboratory, Brookhaven, Conn.) as set forth in Appendix 1. It is to be understood that Appendix 1 forms part of the present application. In the context of Appendix 1, the following abbreviations are used: WAT refers to water or to calcium. Amino acid residues are given in their standard three letter code.

The structure of said Pullulanase is made up of five globular domains, ordered N1, N2, A, B, and C. The domains can be defined as being residues 1–310 for domain N1, 311–420 for Domain N2, residues 421–556 and 596–835 for domain A, residues 557–595 for Domain B, residues 596–922 for Domain C, wherein the numbering refers to the amino acid sequence in SEQ ID NO: 1. Features of Domains N1, A, B and C of particular interest are described below.

Domain N1

Domain N1 contains in this particular pullulanase an extra loop of 100 residues compared to the pullulanase from *Bacillus acidopullulyticus* having the amino acid sequence shown in SEQ ID NO: 5. The loop is also present in the pullulanase from *Bacillus deramificans* having the amino acid sequence shown in SEQ ID NO: 3.

Part of the N2 domain is homologous to the N1 domain of *Pseudomonase amyloderamosa* isoamylase (1bf2.pdb from Brookhaven database).

Domain A

Domain A is the largest domain and contains the active site which comprises a cluster of three amino acid residues, D622, D736 and E651, spatially arranged at the bottom of a cleft in the surface of the enzyme. The structure of Domain A shows an overall fold in common with the α-amylases for which the structure is known, viz. the (beta/alpha) 8 barrel with eight central beta strands (numbered 1–8) and eight flanking a-helices. The β-barrel is defined by McGregor, *J. Prot. Chem.* 7:399, 1988. The C-terminal end of the beta strand 1 is connected to helix 1 by a loop denoted loop 1 and an identical pattern is found for the other loops, although the loops show some variation in size and some can be quite extensive.

The eight central beta-strands in the (beta/alpha) 8 barrel superimpose reasonably well with the known structures of family 13 (Henrissat B. *Biochem. J.* (1991) 280, 309–316 and Henrissat B. and Bairoch A. *Biochem. J.* (1993) 293, 781–788). This part of the structure, including the close surroundings of the active site located at the C-terminal end of the beta-strands, shows a high degree of homology with isoamylases.

In contrast, the loops connecting the beta-strands and alpha helices display a high degree of variation from the known structures of family 13 enzymes. These loops constitute the structural context of the active site, and the majority of the contacts to the substrate is found among residues located in these loops. Distinguishing characteristics such as substrate specificity, substrate binding, pH activity profile, substrate cleavage pattern, and the like, are determined by specific amino acids and the positions they occupy in these loops.

Domain B

Domain B, also referred to as loop 3 of the (beta/alpha) 8 barrel, in comprises amino acid residues 557–595 of the amino acid sequence shown in SEQ ID NO: 1. The most striking difference to other family 13 enzymes being the short amino acid sequence. This short sequence loop are of the same size as the isoamylase loop 3 and spatially positioned close to the active site residues and in close contact to the substrate.

Domain C

Domain C in Promozyme comprises amino acid residues 596–922 of the amino acid sequence shown in SEQ ID NO: 1. Domain C is composed entirely of β-strands which form a single 8-stranded sheet structure that folds back on itself, and thus may be described as a β-sandwich structure. One part of the β-sheet forms the interface to Domain A.

Substrate Binding Site

Parts of the loop discussed above in the context of domains A, B and N2 are of particular interest for substrate interaction and active site reactivity. In particular, in domain A, residues 439–443 in loop 1, residues 490–514 in loop 2, residues 621–628 in loop 4, residues 652–668 in loop 5, residues 679–694 in loop 6, residues 733–740 in loop 7 and residues 787–796 in loop 8; in domain B, residues 553–564 and 581–592 in loop 3; in domain N2, residues 400–404, wherein residue positions correspond to the amino acids in the amino acid sequence in SEQ ID NO: 1.

Homology Building of *Bacillus Deramificans* Pullulanase or Other Pullulanases.

The structure of the *Bacillus deramificans* pullulanase (SEQ ID NO:3) was model built on the structure disclosed in Appendix 1 herein. The structure of other pullulanases may be built analogously.

A model structure of a pullulanase can be built using the Homology program or a comparable program, e.g., Modeller (both from Molecular Simulations, Inc., San Diego, Calif.). The principle is to align the sequence of the pullulanase with the known structure with that of the pullulanase for which a model structure is to be constructed. The structurally conserved regions can then be built on the basis of consensus sequences. In areas lacking homology, loop structures can be inserted, or sequences can be deleted with subsequent bonding of the necessary residues using, e.g., the program Homology. Subsequent relaxing and optimization of the structure should be done using either Homology or another molecular simulation program, e.g., CHARMm from Molecular Simulations.

Methods for Designing Novel Pullulanase Variants

In a first aspect, the present invention relates to a method for producing a variant of a parent pullulanase, wherein the variant has at least one altered property as compared to the parent pullulanase, the method comprising:

i) modeling the parent pullulanase on the three-dimensional structure of SEQ ID NO: 1 depicted in Appendix 1 to produce a three-dimensional structure of the parent pullulanase;

ii) identifying in the three-dimensional structure obtained in step (i) at least one structural part of the parent pullulanase, wherein an alteration in the structural part is predicted to result in an altered property;

iii) modifying the nucleic acid sequence encoding the parent pullulanase to produce a nucleic acid sequence encoding a deletion, insertion, or substitution of one or more amino acids at a position corresponding to the structural part; and iv) expressing the modified nucleic acid sequence in a host cell to produce the variant pullulanase.

The structural part which is identified in step ii) of the method of the invention may be composed of one amino acid residue. Normally, however, the structural part comprises more than one amino acid residue, typically constituting one of the above-mentioned parts of the pullanase structure such as one of the N1, N2, A, B, or C domains, an interface between any of these domains, a calcium binding site, a loop structure, the substrate binding site, or the like.

The structural or functional considerations may involve an analysis of the relevant structure or structural part and its contemplated impact on the function of the enzyme. For example, an analysis of the functional differences between pullulanases and the various isoamylases may be used for assigning certain properties of Promozyme® or homologeous model builded structure to certain parts of the Promozyme® or homologeous model builded structure or to contemplate such relationship. For instance, differences in the pattern or structure of loops surrounding the active site may result in differences in access to the active site of the substrate and thus differences in substrate specificity and/or cleavage pattern.

Furthermore, parts of a pullulanase involved in substrate binding, and thus, for example, substrate specificity and/or cleavage, thermostability, and the like, have been identified (vide infra).

The modification of an amino acid residue or structural region is typically accomplished by suitable modifications of a nucleic acid sequence encoding the parent enzyme in question. The modification may be substitution, deletion or insertion of an amino acid residue or a structural part.

The property to be modified may be stability (e.g. thermostability), pH dependent activity, substrate specificity, such as decreased condensation reactions, isoamylase like activity etc. Thus, the altered property may be an altered specific activity at a given pH and/or altered substrate specificity, such as an altered pattern of substrate cleavage or an altered pattern of substrate inhibition.

In step ii) of the method according to the invention the part of the structure to be identified is preferably one which in the folded enzyme is believed to be in contact with the substrate (cf. the disclosure above in the section entitled "Substrate Binding Site") or involved in substrate specificity and/or cleavage pattern, and/or one which is contributing to the pH or temperature profile of the enzyme, or is otherwise responsible for the properties of the pullulanase.

Described in the following are specific types of variants which have been designed by use of the method of the invention.

The variants of the invention may comprise additional modifications in addition to the modifications described herein. The variants preferably have an amino acid sequence having more than 40% homology with SEQ ID NO: 1, SEQ ID NO: 3, or SEQ ID NO: 5, preferably more than 50%, e.g. more than 60%, such as more than 70%, more than 75%, more than 80%, more than 85%, more than 90%, more than 91%, more than 92%, more than 93%, more than 94%, more than 95%, more than 96%, more than 97%, more than 98% or more than 99% homology with the amino acid sequences shown in SEQ ID NO: 1, SEQ ID NO: 3 or SEQ ID NO: 5.

In the present context the term "homologous to" or "homology" (also sometimes referred to as "similarity") is used in it conventional meaning and the "homology" between two amino acid sequences may be determined by use of any conventional algorithm, preferably by use of the GAP program from the UWGCG package using default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, *Journal of Molecular Biology*, 48, 443–445 (1970).

As mentioned above, the property to be modified may be stability (e.g. thermostability), pH dependent activity, substrate specificity, such as increased isoamylase activity, or specific activity. Thus, the altered property may be an altered specific activity at a given pH and/or an altered substrate specificity, such as an altered pattern of substrate cleavage or an altered pattern of substrate inhibition.

In a particular interesting embodiment of the invention the property to be modified is the thermostability of the enzyme.

In the present context, the term "thermostable" (or "thermostability") refers in general to the fact that the pullulanase variants according to the invention have an improved thermostability compared to the relevant parent pullulanase. The degree of improvement in thermostability can vary according to factors such as the thermostability of the parent pullulanase and the intended use of the pullulanase variant, i.e. whether it is primarily intended to be used for liquefaction or for saccharification or both. It will be apparent from the discussion below that for saccharification, the enzyme variant should maintain a substantial degree of enzyme activity during the saccharification step at a temperature of at least about 63° C., preferably at least about 70° C., while an enzyme variant designed for use in the liquefaction step should be able to maintain a substantial degree of enzyme activity at a temperature of at least about 95° C.

The improved thermostability of enzyme variants according to the invention can in particular be defined according to one or more of the following criteria:

In one embodiment, the pullulanase variant of the invention has an improved thermostability (and/or the method of the invention provides a pullulanase with an improved thermostabilty) as defined by differential scanning calorimetry (DSC) using the method described herein.

In another embodiment, the pullulanase variant of the invention has an improved thermostability (and/or the method of the invention provides a pullulanase with an improved thermostabilty) as defined by an increased half-time ($T_{1/2}$) of at least about 5%, preferably at least about 10%, more preferably at least about 15%, more preferably at least about 25%, most preferably at least about 50%, such as at least about 100%, in the "$T_{1/2}$ assay for liquefaction" described herein, using a pH of 5.0 and a temperature of 95° C. Pullulanase variants according to this definition are suitable for use in the liquefaction step of the starch conversion process.

Alternatively or additionally, a pullulanase variant suitable for use in liquefaction can be defined as having an improved thermostability as defined by an increased residual enzyme activity of at least about 5%, preferably at least about 10%, more preferably at least about 15%, more preferably at least about 25%, most preferably at least about 50%, such as at least about 100%, in the "assay for residual activity after liquefaction" described herein, using a pH of 5.0 and a temperature of 95° C.

In a further embodiment, the enzyme variant of the invention has an improved thermostability (and/or the method of the invention provides a pullulanase with an improved thermostabilty) as defined by an increased half-time ($T_{1/2}$) of at least about 5%, preferably at least about 10%, more preferably at least about 15%, more preferably at least about 25%, most preferably at least about 50%, such as at least about 100%, in the "$T_{1/2}$ assay for saccharification" described herein, using a pH of 4.5 and a temperature of 70° C. Such variants are suitable for use in the saccharification step of the starch conversion process.

Alternatively or additionally, a pullulanase variant suitable for saccharification can be defined as having an improved thermostability as defined by an increased residual enzyme activity of at least about 5%, preferably at least about 10%, more preferably at least about 15%, more preferably at least about 25%, most preferably at least about 50%, such as at least about 100%, in the "assay for residual activity after saccharification" described herein, using a pH of 4.5 and a temperature of 63° C. Preferably, this improved thermostability is also observed when assayed at a temperature of 70° C.

The term "substantially active" as used herein for a given pullulanase variant and a given set of conditions of temperature, pH and time means that the relative enzymatic activity of the enzyme variant is at least about 25%, preferably at least about 50%, in particular at least about 60%, especially at least about 70%, such as at least about 90% or 95%, e.g. at least about 99% compared to the relative activity of the parent enzyme tested under the same set of conditions.

One advantage of the thermostable pullulanase of the invention is that they make it possible to perform liquefaction and debranching simultaneously before the saccharification step. This has not previously been possible, since the known pullulanases with acceptable specific activity are thermolabile and are inactivated at temperatures above 60° C. (Some thermostable pullulanases from Pyrococcus are known, but these have an extremely low specific activity at higher temperatures and are thus unsuitable for purposes of the present invention). By debranching, using the thermostable pullulanases of the invention, during liquefaction together with the action of an α-amylase, the formation of panose precursors is reduced, thereby reducing the panose content in the final product and increasing the overall saccharification yield. It is also possible in this manner to extend the liquefaction process time without risking formation of large amount of panose precursors. By prolonging the liquefaction step, the DE yield is increased from 10–15 to e.g. 15–20, reducing the need for glucoamylase. This reduced glucoamylase requirement is in turn advantageous as the formation of undesired isomaltose is reduced, thereby resulting in an increased glucose yield. In addition, the reduced glucoamylase addition enables the saccharification step to be carried out at a higher substrate concentration (higher DS, dry substances, concentration) than the normal approx. 30–35% used according to the prior art. This allows reduced evaporation costs downstream, e.g. in a high fructose corn syrup process, and the saccharification reaction time can also be reduced, thereby increasing production capacity. A further advantage is that α-amylase used in the liquefaction process does not need to be inactivated/denatured in this case.

Furthermore, it is also possible to use the thermostable pullulanases of the invention during saccharification, which is advantageous for several reasons. In the conventional starch saccharification process, the process temperature is not more than 60° C. due to the fact that neither the saccharification enzyme pullulanase nor AMG™ are sufficiently thermostable to allow the use of a higher temperature. This is a disadvantage, however, as it would be very desirable to run the process at a temperature of above about 60° C., in particular above 63° C., e.g. about 70° C., to reduce microbial growth during the relatively long saccharification step. Furthermore, a higher process temperature normally gives a higher activity per mg of enzyme (higher specific activity), thereby making it possible to reduce the weight amount of enzyme used and/or obtain a higher total enzymatic activity. A higher temperature can also result in a higher dry matter content after saccharification, which would be beneficial in terms of reducing evaporation costs.

In another interesting embodiment of the invention the property to be modified is the substrate specificity of the pullulanase, in particular to modify the substrate specificity of the pullulanase in such a way the variant pullulanase becomes more "isoamylase-like" in the sense of having an increased activity towards high molecular weight branched starchy material such as glycogen and amylopectin. Methods for determining the substrate specificity of pullulanases are discussed in the following section entitled "Methods for determing stability, activity and specificity".

Thus, when used herein, the term "increased isoamylase activity" refers in general to the fact that the pullulanase variants according to the invention exhibits a higher activity towards high molecular weight branched starchy material, such as glycogen and amylopectin as compared to the parent pullulanase.

The increased isoamylase activity of the pullulanase variants according to the invention can in particular be defined according to the below criteria:

In one embodiment the pullulanase variant according to the invention has an increased isoamylase activity as defined by an increase of at least 5%, preferably of at least 10%, more preferably of at least 15%, more preferably of at least 25%, most preferably of at least 50%, in particular of at least 75%, such as of at least 100% in the number of reducing ends formed in the "assay for isoamylase-like activity" described herein, using 50 mM sodium acetate, a pH of 4.5, 5.0 or 5.5, a temperature of 60° C. and when incubated with a 10 w/v rabbit liver glycogen solution for a period of 10 min.

In the present context the term "pullulanase activity" is intended to mean that the pullulanase variant in question is capable of degrading pullulan when tested as described in the Examples (see the section entitled "Determination of pullulanase activity").

Methods for Determining Stability, Activity and Specificity

Thermostability

Thermostability of pullulanases can be detected by measuring the residual activity by incubating the enzyme under accelerated stress conditions, which comprise: pH 4.5 in a 50 mM sodium acetate buffer without a stabilizing dextrin matrix (such as the approximately 35% dry matter which is normally present during saccharification). The stability can be determined at isotherms of e.g. 63° C., 70° C., 80° C., 90° C. and 95° C., measuring the residual activity of samples taken from a water bath at regular intervals (e.g. every 5 or 10 min.) during a time period of 1 hour. For determining stability for the purpose of liquefaction, a pH of 5.0, a temperature of 95° C. and a total assay time of 30 to 120 minutes are used ("assay for residual activity after liquefaction"). For determining stability for the purpose of saccharification, a pH of 4.5, a temperature of 63° C. or 70° C. and a total assay time of 30 minutes are used ("assay for residual activity after saccharification").

Alternatively, the thermostability may be expressed as a "half-time" ($T_{1/2}$), which is defined as the time, under a given set of conditions, at which the activity of the enzyme being assayed is reduced to 50% of the initial activity at the beginning of the assay. In this case, the "$T_{1/2}$ assay for liquefaction" uses a pH of 5.0 and a temperature of 95° C., while the "$T_{1/2}$ assay for saccharification" uses a pH of 4.5 and a temperature of 70° C. The assay is otherwise performed as described above for the respective assays for residual activity.

Activity: Somogyi-Nelson Method for Determination of Reducing Sugars

The activity of pullulanases can be measured using the Somogyi-Nelson method for the determination of reducing sugars (*J. Biol. Chem.* 153, 375 (1944)). This method is based on the principle that sugar reduces cupric ions to cuprous oxide, which reacts with an arsenate molybdate reagent to produce a blue colour that is measured spectrophotometrically. The solution to be measured must contain 50–600 mg of glucose per liter. The procedure for the Somogyi-Nelson method is as follows:

Sample value: Pipet 1 ml of sugar solution into a test tube. Add 1 ml of copper reagent. Stopper the test tube with a glass bead. Place the test tube in a boiling water bath for 20 minutes. Cool the test tube. Add 1 ml of Nelson's color reagent. Shake the test tube without inverting it. Add 10 ml of de-ionized water. Invert the test tube and shake vigorously. Measure the absorbance at 520 nm, inverting the test tube once immediately prior to transfer of the liquid to the cuvette.

Blank value: Same procedure as for the sample value, but with water instead of sugar solution.

Standard value: Same procedure as for the sample value.

Calculations: In the region 0–2 the absorbance is proportional to the amount of sugar.

$$\text{mg sugar/l} = \frac{100(\text{sample} - \text{blank})}{(\text{standard} - \text{blank})}$$

$$\% \text{ glucose} = \frac{(\text{sample} - \text{blank})}{100 \times (\text{standard} - \text{blank})}$$

Reagents:

1. Somogyi's Copper Reagent 35.1 g $Na_2HPO_4.2H_2O$ and 40.0 g potassium sodium tartrate ($KNaC_4H_4O_2.4H_2O$) are dissolved in 700 ml of de-ionized water. 100 ml of 1N sodium hydroxide and 80 ml of 10% cupric sulphate ($CuSO_4.5H_2O$) are added. 180 g of anhydrous sodium sulphate are dissolved in the mixture, and the volume is brought to 1 liter with de-ionized water.

2. Nelson's Color Reagent 50 g of ammonium molybdate are dissolved in 900 ml of de-ionized water. Then 42 ml of concentrated sulphuric acid are added, followed by 6 g of disodium hydrogen arsenate heptahydrate dissolved in 50 ml of deionized water, and the volume is brought to 1 litre with deionized water. The solution is allowed to stand for 24–48 hours at 37° C. before use and is stored in the dark in a brown glass bottle with a glass stopper.

3. Standard 100 mg of glucose (anhydrous) are dissolved in 1 liter of de-ionized water.

Alternatively, the release of reducing sugars can be measured using a 96 well plate set-up modified after Fox, J. D. & Robyt, J. F. (1991) Anal. Biochem. 195, 93–96. Assay conditions are (in brief): 1 ml substrate (e.g. 1% solution) in 50 mM citric acid pH 5 is preincubated at 60° C. A zero timepoint is taken 150 µl sample and transferred to a microtiter plate well containing 150 µl solution A+B for reducing sugar determination. The enzymatic reaction is initiated by addition of 100 µl enzyme and time points are taken at T=1,2,3,4, and 5 min.

After completion of the assay, the plate is developed by incubation at 85° C. for 70 minutes and the plate is read at 540 nm.

Reagents for determination of reducing value: Solution A) and solution B (62 mg copper sulfate pentahydrate and 63 mg L-serine in 50 ml water).

Pullulanase Specificity

Methods for the determination and characterization of the profile of action and specificity of pullulanases for various substrates (e.g. amylopectin, glycogen and pullulan) are described by Kainuma et al. in *Carbohydrate Research*, 61 345–357 (1978). Using these methods, the relative activity of a pullulanase can be determined, and the relative activity of a pullulanase variant according to the invention compared to the relative activity of the parent pullulanase can be assessed, for example to determine whether a pullulanase variant has the desired increased specificity toward high molecular weight saccharides, such as amylopectin, compared to the parent pullulanase.

In order to determine whether the pulluanase variant possesses an increased isoamylase activity as compared to the parent pullulanse the following test may be performed ("assay for isoamylase-like activity"):

1000 mg rabbit liver glycogen is dissolved in 40 ml water to which 0.2% NaOH has been added. 800 mg $NaBH_4$ is added carefully under stirring. The solution is stirred for 48 hours at 25° C. after which the reaction is stopped by addition of Amberlite IR-118H (a cation exchanger which removes the boron ions and hence stops the reaction). The solution is filtered to remove the matrix and evaporated to give 10 ml. The solution is then dialyzed extensively against de-ionized water to remove residual boron ions. The parent pullulanase and the pulluanase variant are assayed according to the method of Somogyi-Nelson, using 50 mM sodium acetate, pH values of 4.5, 5.0 or 5.5 and a temperature of 60° C., with a reaction time of 10 minutes. Glucose is used as a standard, a standard curve being made from solutions containing of 0–200 mg glucose/liter.

Clearly, the higher the number of reducing ends formed during the incubation period, the higher "isoamylase activity". The increase in the pullulanase variant's isoamylase activity is expressed as a percentage value based on the original "isoamylase activity" of the parent pullulanase.

Pullulanase Variants with Altered Stability

A variant with improved stability (typically increased thermostability) may be obtained by substitution with proline, substitution of histidine with another amino acid, introduction of a disulfide bond, removal of a deamidation site, altering a hydrogen bond contact, filling in an internal structural cavity with one or more amino acids with bulkier side groups, introduction of interdomain interactions, altering charge distribution, helix capping, or introduction of a salt bridge.

Increased Mobility Regions:

The following regions have an increased mobility in the crystal structure of Promozyme®, and it is presently believed that these regions can be responsible for stability or activity of the enzyme. Improvements of the enzyme can be obtained by mutation in the below regions and positions. Introducing e.g. larger residues or residues having more atoms in the side chain could increase the stability, or e.g. introduction of residues having fewer atoms in the side chain could be important for the mobility and thus the activity profile of the enzyme. The regions can be found by analysing the B-factors taken from the pdb file, and/or from molecular dynamics calculations of the isotropic fluctuations. These can be obtained by using the program CHARMm from MSI (Molecular simulations inc.).

Thus, in order to stabilize mobile regions in the structure, a preferred variant of a parent pullulanase comprises a modification, e.g. a substitution, of an amino acid residue corresponding to one or more of the following residues of the amino acid sequence set forth in SEQ ID NO: 1:

408–429 (i.e. 408, 409, 410, 411, 412, 413, 414, 415, 416, 417, 418, 419, 420, 421, 422, 423, 424, 425, 426, 427, 428 and 429), 300–314 (i.e. 300, 301, 302, 303, 304, 305, 306, 307, 308, 309, 310, 311, 312, 313 and 314), 157–165 (i.e. 157, 158, 159, 160, 161, 162, 163, 164 and 165), 95–113 (i.e. 95, 96, 97, 98, 99, 100, 101, 102, 103, 104, 105, 106, 107, 108, 109, 110, 111, 112 and 113), 130–140 (i.e. 130, 131, 132, 133, 134, 135, 136, 137, 138, 139 and 140), 232–238 (i.e. 232, 233, 234, 235, 236, 237 and 238), 266–272 (i.e. 266, 267, 268, 269, 270, 271 and 272), 302–308 (i.e. 302, 303, 304, 305, 306, 307 and 308), 418–428 (i.e. 418, 419, 420, 421, 422, 423, 424, 425, 426, 427 and 428), 500–507 (i.e. 500, 501, 502, 503, 504, 505, 506 and 507), 659–665 (i.e. 659, 660, 661, 662, 663, 664 and 665) and 751–755 (i.e. 751, 752, 753, 754 and 755).

Similar modifications, e.g. substitutions, may be introduced in equivalent positions of other pullulanases. Variants of particular interest have a combination of one or more of the above with any of the other modifications disclosed herein.

For example, other preferred modifications, e.g. substitutions, which are believed to stabilized mobile regions in the structure of the pullulanase from *Bacillus deramificans*, correspond to one or more of the following residues of the amino acid sequence set forth in SEQ ID NO: 3:

406–427 (i.e. 406, 407, 408, 409, 410, 411, 412, 413, 414, 415, 416, 417, 418, 419, 420, 421, 422, 423, 424, 425, 426 and 427), 298–312 (i.e. 298, 299, 300, 301, 302, 303, 304, 305, 306, 307, 308, 309, 310, 311 and 312), 153–161 (i.e. 153, 154, 155, 156, 157, 158, 159, 160 and 161), 91–109 (i.e. 91, 92, 93, 94, 95, 96, 97, 98, 99, 100, 101, 102, 103, 104, 105, 106, 107, 108 and 109), 126–136 (i.e. 126, 127, 128, 129, 130, 131, 132, 133, 134, 135 and 136), 230–236 (i.e. 230, 231, 232, 233, 234, 235 and 236), 264–270 (i.e. 264, 265, 266, 267, 268, 269 and 270), 300–306 (i.e. 300, 301, 302, 303, 304, 305 and 306), 416–426 (i.e. 416, 417, 418, 419, 420, 421, 422, 423, 424, 425 and 426), 498–505 (498, 499, 500, 501, 502, 503, 504 and 505), 656–662 (i.e. 656, 657, 658, 659, 660, 661 and 662) and 749–753 (i.e. 749, 750, 751, 752 and 753).

Furthermore, it is envisaged from the structure that deletion of certain amino acid residues will confer increased stability, such as increased thermostability, to the thus produced variant. Variants, which are believed to be of particular importance, comprises a deletion of amino acid residues corresponding to the following residues of the amino acid sequence set forth in SEQ ID NO: 1:

Deletion of the peptide fragment 158–275, such as a deletion starting from position 158, 159, 160 or 161 and ending at position 270, 271, 272, 273, 274 or 275, i.e. the longest deletion will be deletion of the peptide fragment 158–275 and the shortest deletion will be deletion of the peptide fragment 161–270.

Other deletions which are expected to confer increased stability, such as increased thermostability, to the pullulanase variant comprises a deletion of amino acid residues corresponding to the following residues of the amino acid sequence set forth in SEQ ID NO: 1:

Deletion of the peptide fragment 1–315, such as deletion of the peptide fragment 1–314, 1–313, 1–312, 1–311, 1–310, 1–309, 1–308, 1–307, 1–306, 1–305, or 1–304.

Furthermore, the following deletions are expected to confer increased stability, such as increased thermostability, to the pullulanase variant comprises a deletion of amino acid residues corresponding to the following residues of the amino acid sequence set forth in SEQ ID NO: 1:

Deletion of the peptide fragment 1–115, such as deletion of the peptide fragment 1–114, 1–113, 1–112, 1–111, 1–110, 1–109, 1–108, 1–107, 1–106 or 1–105.

Similar deletions may be introduced in equivalent positions of other pullulanases. Variants of particular interest have a combination of one or more of the above with any of the other modifications disclosed herein.

For example, it is envisaged that deletion of the below amino acid residues will confer increased stability, such as increased thermostability, to the thus produced variant of the pullulanase from *Bacillus deramificans* (SEQ ID NO: 3):

Deletion of the peptide fragment 154–273, such as a deletion starting from position 154, 155, 156 or 157 and ending at position 268, 269, 270, 271, 272 or 273, i.e. the longest deletion will be deletion of the peptide fragment 154–273 and the shortest deletion will be deletion of the peptide fragment 157–268.

Other deletions which are expected to confer increased stability, such as increased thermostability, to the pullulanase variant comprises a deletion of amino acid residues corresponding to the following residues of the amino acid sequence set forth in SEQ ID NO: 3:

Deletion of the peptide fragment 1–313, such as deletion of the peptide fragment 1–312, 1–311, 1–310, 1–309, 1–308, 1–307, 1–306, 1–305, 1–304, or 1–303.

Furthermore, the following deletions are expected to confer increased stability, such as increased thermostability, to the pullulanase variant comprises a deletion of amino acid residues corresponding to the following residues of the amino acid sequence set forth in SEQ ID NO: 3:

Deletion of the peptide fragment 1–111, such as deletion of the peptide fragment 1–111, 1–110, 1–109, 1–108, 1–107, 1–106, 1–105, 1–104, 1–103, 1–102 or 1–101.

Cavities and Crevices

The structure of the pullulanase contains a number of unique internal cavities, which may contain water, and a number of crevices. In order to increase the stability, preferably the thermostability, of the pullulanase it may be desirable to reduce the number or size of cavities and crevices, e.g., by introducing one or more hydrophobic contacts, preferably achieved by introducing amino acids with bulkier side chains in the vicinity or surroundings of the cavity or crevice. For instance, the amino acid residues to be modified are those which are involved in the formation of a cavity or crevice.

In order to determine which amino acid residues of a given enzyme are involved in the formation of cavities or crevices the Conolly program is normally used (B. Lee and F. M. Richards, *J. Mol. Biol.* 55, 379–400 (1971)). The program uses a probe with a certain radius to search the external and internal surface of the protein. The smallest crevice observable in this way has the probe radius.

To analyze the solved structure of Promozyme®, a modified version of the Connolly program included in the program of INSIGHT was used. In the first step, the water molecules and the ions were removed by unmerging these atoms from the solved structure. By using the command MOLECULE SURFACE SOLVENT the solvent accessible surface area was calculated for all atoms and residues using a probe radius of 1.4 Å, and displayed graphically together with the model of the solved structure. The internal cavities are then seen as dot surfaces with no connections to the external surface.

Suggestions for specific modifications to fill out the cavities are given below. By using the homology built structures and/or comparisons based on sequence alignment, mutations for homologous structures of pullulanases can be made.

Accordingly, in a further aspect the present invention relates to a method for constructing a variant of a parent pullulanase, the method comprising:

a) identifying an internal cavity or crevice in the three-dimensional structure of the parent pullulanase;
b) substituting at least one amino acid residue involved in the formation of a cavity or crevice with another amino acid residue which increases the hydrophobic interaction and/or fills out or reduces the size of the cavity or crevice;
c) optionally repeating steps a) and b) recursively;
d) optionally, making alterations each of which is an insertion, a deletion or a substitution of an amino acid residue at one or more positions other than b);
e) preparing the variant resulting from steps a)–d);
f) testing the stability and/or the temperature dependent activity profile of the variant; and
g) optionally repeating steps a)–f) recursively; and
h) selecting a variant having increased stability and/or an altered temperature dependent activity profile as compared to the parent pullulanase.

In a preferred embodiment of the invention the variant pullanase provided by the above method have increased thermostability as compared to the parent pullulanase. The thermostability of a given variant may be assessed as described in the above section entitled "Methods for determining stability, activity and specificity".

It will be understood that the cavity or crevice is identified by the amino acid residues surrounding said cavity or crevice, and that modification of said amino acid residues are of importance for filling or reducing the size of the cavity or crevice. Preferably, the modification is a substitution with a bulkier amino acid residue, i.e. one with a greater side chain volume or with an increased number of atoms in the side chain. For example, all the amino acids are bulkier than Gly, whereas Tyr and Trp are bulkier than Phe. The particular amino acid residues referred to below are those which in a crystal structure have been found to flank the cavity or crevice in question.

In a preferred embodiment, the variant of a pullulanase, in order to fill, either completely or partly, cavities or crevices located internally or externally in the structure, comprises a modification, e.g. a substitution, of an amino acid residue corresponding to one or more of the following residues of the amino acid sequence set forth in SEQ ID NO: 1:

406, 394, 568, 573 576, 563, 557, 396, 392, 515, 583, 442, 792, 767, 732, 760, 783, 740, 688,478, 534, 550, 627, 314.

In a more preferred embodiment, the variant of a pullulanse comprises one or more substitutions corresponding to the following substitutions in the amino acid sequence set forth in SEQ ID NO: 1:

G406A, P394F/W/I/L, I568L/F, Y573W, T576N/L/I, S563T, T557N, A396V/L/I, V392, N515M/L/I, V583I/F/L, D442Q, S792Y/F, V767Q/E/L/I, V732I/L, D760Q/E/F/Y, L783F/Y, L740Q, D688Y/F/E/Q/R/K, L478Q/R, L534F/Y/I, M550F/Y/I/L, L627F/Y/I, L314I.

Similar modifications, e.g. substitutions, may be introduced in equivalent positions of other pullulanases. Variants of particular interest have a combination of one or more of the above with any of the other modifications disclosed herein.

For example, the variant of a pullulanase may also comprise one or more substitutions corresponding to the following substitutions in the amino acid sequence set forth in SEQ ID NO: 3:

566, 485, 487, 437, 775, 779, 551, 428, 492, 495, 392, 621, 437+503, 674+664 and 823.

In a more preferred embodiment, the variant of a pullulanse comprises one or more substitutions corresponding to the following substitutions in the amino acid sequence set forth in SEQ ID NO: 3:

I566A, Q485H, M487L, D437H, Q775H, E779D, V551I, I428Y/F, S492F, V495I/F/Y, P392Y, L621Q, D437H+D503Y, V674+L664F and L823V.

Disulfide Bonds

A variant with improved stability (typically improved thermostability) as compared to the parent pullulanase may be obtained by introducing new interdomain and intradomain contacts, such as establishing inter- or intradomain disulfide bridges.

Accordingly, a further aspect of the present invention relates to a method for constructing a variant of a parent pullulanase, the method comprising:

a) identifying in the three-dimensional structure of the parent pullulanase two or more amino acid residues which, when substituted with cysteines, are capable of forming a disulfide bond;
b) substituting the amino acids identified in a) with cysteines;
c) optionally repeating steps a) and b) recursively;
d) optionally, making alterations each of which is an insertion, a deletion or a substitution of an amino acid residue at one or more positions other than b);
e) preparing the variant resulting from steps a)–d);
f) testing the stability of said variant; and
g) optionally repeating steps a)–f) recursively; and
h) selecting a variant having increased stability as compared to the parent pullulanase.

In a preferred embodiment of the invention the variant pullanase provided by the above method have increased thermostability as compared to the parent pullulanase. The thermostability of a given variant may be assessed as described in the above section entitled "Methods for determining stability, activity and specificity".

In order to determine, in the three-dimensional structure of the parent pullulanase, the amino acid residues which, when substituted with cysteines, are capable of forming a disulfide bond, residues with CB atoms less than 4 Å from each other, and where the direction of the CA–CB from each residue is pointing towards the other residue are identified. Following the above-mentioned guidelines, the below amino acid residues were identified in the amino acid sequence of SEQ ID NO: 1, and it is contemplated that these residues are suitable for cystein replacement, thereby opening up the possibility of establishing one or more disulfide bridges in the variant pullulanase:

K758C+I914C, T916C+A765C, I897C+S819C, P525C+E499C, H286C+T148C.

Similar substitutions may be introduced in equivalent positions of other pullulanases. Variants of particular interest have a combination of one or more of the above with any of the other modifications disclosed herein.

For example, it is contemplated that the following residues, identified in the amino acid 20 sequence of the pullulanase from *Bacillus deramificans* (SEQ ID NO: 3), are suitable for cystein replacement, thereby opening up the possibility of establishing one or more disulfide bridges in the variant pullulanase:

K756C/I912C, M914C/A763C, V895C/G817C, A523C/E497C, H284C/T144C.

Surface Charge Distribution

A variant with improved stability (typically improved thermostability) as compared to the parent pullulanase may be obtained by changing the surface charge distribution of the pullulanase. For example, when the pH is lowered to about 5 or below histidine residues typically become positively charged and, consequently, unfavorable electrostatic interactions on the protein surface may occur. By engineering the surface charge of the pullulanase one may avoid such unfavorable electrostatic interactions which in turn leads to a higher stability of the pullulanase.

Therefore, a further aspect of the present invention relates to method for constructing a variant of a parent pullulanase, the method comprising:

a) identifying, on the surface of the parent pullulanase, at least one amino acid residue selected from the group consisting of Asp, Glu, Arg, Lys and His;
b) substituting, on the surface of the parent pullulanase, at least one amino acid residue selected from the group consisting of Asp, Glu, Arg, Lys and His with an uncharged amino acid residue;
c) optionally repeating steps a) and b) recursively;
d) optionally, making alterations each of which is an insertion, a deletion or a substitution of an amino acid residue at one or more positions other than b);
e) preparing the variant resulting from steps a)–d);
f) testing the stability of said variant; and
g) optionally repeating steps a)–f) recursively; and
h) selecting a variant having increased stability as compared to the parent pullulanase.

As will be understood by the skilled person it may also, in some cases, be advantageous to substitute an uncharged amino acid residue with an amino acid residue bearing a charge or, alternatively, it may in some cases be advantageous to substitute an amino acid residue bearing a charge with an amino acid residue bearing a charge of opposite sign. Thus, the above-mentioned method may easily be employed by the skilled person also for these purposes. In the case of substituting an uncharged amino acid residue with an amino acid residue bearing a charge the above-mentioned method may be employed the only difference being steps a) and b) which will then read:

a) identifying, on the surface of the parent pullulanase, at least one uncharged amino acid residue;
b) substituting, on the surface of the parent pullulanase, at least one uncharged amino acid residue with a charged amino acid residue selected from the group consisting of Asp, Glu, Arg, Lys and His.

Also in the case of changing the sign of an amino acid residue present on the surface of the pullulanase the above method may be employed. Again, compared to the above method, the only difference being steps a) and b) which, in this case, read:

a) identifying, on the surface of the parent pullulanase, at least one charged amino acid residue selected from the group consisting of Asp, Glu, Arg, Lys and His;
b) substituting, on the surface of the parent pullulanase, at least one charged amino acid residue identified in step a) with an amino acid residue having an opposite charge.

Thus, Asp may be substituted with Arg, Lys or His; Glu may be substituted with Arg, Lys or His; Arg may be substituted with Asp or Glu; Lys may be substituted with Asp or Glu; and His may be substituted with Asp or Glu.

In a preferred embodiment of the invention the variant pullulanase provided by the above method(s) have increased thermostability as compared to the parent pullulanase. The thermostability of a given variant may be assessed as described in the above section entitled "Methods for determining stability, activity and specificity".

In order to determine the amino acid residues of a pullulanase, which are present on the surface of the enzyme, the surface accessible area are measured using the DSSP program (Kabsch and Sander, *Biopolymers* (1983), 22, 2577–2637). All residues having a surface accessibilty higher than 0 is regarded a surface residue.

The amino acid residues found on the surface of Promozyme® using the above method are as follows:

E526, Q544, E760, N338, N228, N181, and it is contemplated that the following substitutions are of particular interest:

E526H, Q544E, E760Q, N338K/R, N228DE/, N181K/R.

Similar substitutions may be introduced in equivalent positions of other pullulanases. Variants of particular interest have a combination of one or more of the above with any of the other modifications disclosed herein.

For example, the variant of a pullulanase may also comprise one or more modifications, e.g. substitutions, corresponding to the following substitutions in the amino acid sequence set forth in SEQ ID NO: 3:

444, 530, 710 and 855.

In a more preferred embodiment, the variant of a pullulanse comprises one or more substitutions corresponding to the following substitutions in the amino acid sequence set forth in SEQ ID NO: 3:

D444R/K, K530Y/F/L, N710R and T855K.

Other Modifications

Variants with improved stability, in particular variants with improved thermostability, can be obtained by improving existing or introducing new interdomain or intradomain contacts. Such improved stability can be achieved by the modifications listed below.

Thus, one preferred embodiment of the invention relates to a variant of a parent pullulanase which has an improved stability and one or more salt bridges as compared to the parent pullulanase, wherein said variant comprises a modifications, e.g. a substitution, in a position corresponding to at least one of the following sets of positions in SEQ ID NO: 1:

301, 385, 298, 299, 385 and 299+385, in particular L301R, N385R, H298R, N299R, N385D and N299R+N385D.

Similar modifications, e.g. substitutions, may be introduced in equivalent positions of other pullulanases. Variants of particular interest have a combination of one or more of the above with any of the other modifications disclosed herein.

For example, it is contemplated that the following substitutions in the pullunanase having the amino acid sequence set forth in SEQ ID NO: 3 will enhance the stability of the enzyme: T891D, S892K, T891D+S892K and N400R.

In another preferred embodiment, the variant of the pullulanase comprises a substitution corresponding to one or more of the following substitutions with proline in the amino acid sequence set forth in SEQ ID NO: 1:

G293P, K151P, K122P, N315P, N374P, N793P, A446P, G672P, G668P, T556P

In a further interesting embodiment of the invention, the variant of the pullulanase comprises a substitution corresponding to one or more of the following substitutions with proline in the amino acid sequence set forth in SEQ ID NO: 3:

D562P, G794P, G292P, D148P, N119P, D314P, N373P, N792P, G671P, G667P and T554P.

Analogously, it may be preferred that one or more histidine residue(s) present in the parent pullulanase is (are) substituted with a non-histidine residues such as Y, V I, L, F, M, E, Q, N, or D. Accordingly, in another preferred embodiment, the variant of the parent pullulanase comprises a substitution of an amino acid residue corresponding to one or more of the following residues of the amino acid sequence set forth in SEQ ID NO: 3: H422Y/F/L, H483Y/F/L, H543Y/F/L/N and H613Y/F/L.

It may be preferred that one or more asparagine or glutamine residues present in the parent pullulanase is or are substituted with a residue lacking the amide group on the side chain. Preferably, such asparagines or glutamine residues are substituted with S, T, V, L and/or F amino acid residues. Accordingly, in another preferred embodiment, the variant of the parent pullulanase comprises a modification, e.g. a substitution, of an amino acid residue corresponding to one or more of the following residues of the amino acid sequence set forth in SEQ ID NO: 1:

Q543, Q339, N337, Q380, Q353, N384, N286, N298, N227, Q227, Q210, N180, Q259, N583, N790, N793, N505, N788, N736, N684, N689 or N681, preferably Q543S/T/V/L/F, Q339S/T/V/L/F, N337S/T/V/L/F, Q380S/T/V/L/F, Q353S/T/V/L/F, N384S/T/V/L/F, N286S/T/V/L/F, N298S/T/V/L/F, N227S/T/V/L/F, Q227S/T/V/L/F, Q210S/T/V/L/F, N180S/T/V/L/F, Q259S/T/V/L/F, N583S/T/V/L/F, N790S/T/V/L/F, N793S/T/V/L/F, N505S/T/V/L/F, N788S/T/V/L/F, N736S/T/V/L/F, N684S/T/V/L/F, N689S/T/V/L/F and N681S/T/V/L/F.

The corresponding residues found in the pullulanase from *Bacillus deramificans* (SEQ ID NO: 3) include:

N400, N446, N504, N717, N735 and N789, preferably N400S/T/V/L/F, N446S/T/V/L/F, N504S/T/V/L/F, N717S/T/V/L/F, N735S/T/V/L/F and N789S/T/V/L/F.

Moreover, it is contemplated that modifications, e.g. substitutions, in the region linking the N2 and the A domain, as well as other regions linking other domains, will confer additional stability, such as an increased thermostability, to the enzyme. Thus, in an interesting embodiment of the invention, the pullulanase variant comprises one or more modifications, e.g. substitutions, in the domain-linking regions (e.g. the region linking the N2 and A domains).

Examples of such substitutions include one or more of the following substitutions in the pullulanase from *Bacillus deramificans* (SEQ ID NO: 3):

111, 112,

158–160 (i.e. 158, 159 and 160),

270–274 (i.e. 270, 271, 272, 273 and 274),

302–314 (i.e. 302, 303, 304, 305, 306, 307, 308, 309, 310, 311, 312, 313 and 314) and 408–426 (i.e. 408, 409, 410, 411, 412, 413, 414, 415, 416, 417, 418, 419, 420, 421, 422, 423, 424, 425 and 426).

Examples of specific substitutions are: S111T/V/L, N112S/T/Q, S158Y/F/T, L159Y/K/R/A/S/T, G160A/S/T, D270E/S/T, L271V/I, V272I, T273N/D/E/Y/F, V274I, N302V/L/Y, N305V/L/Y, S306T/V, Q308K/R/A/S/T, Y309F, Y310E/D/Q/N/L/V/I, D314A/S/T, L409N, D408S/T, A410S/T, D413R/K/S/T, A415S/T, G416S/T/V, N418A/V/S/T, S419D/N/T, K421E/Q/S/T/V/A, H422D/L/Y/F, I423L/V/S/T/N/Q, T424S/A and K426A/S/T.

Other substitutions which are considered of particular importance in SEQ ID NO:3 include D437N and D440N.

Similar modifications, e.g. substitutions, may be introduced in equivalent positions of other pullulanases. Modifications of particular interest are any combination of one or more of the above with any of the other modifications disclosed herein.

Before actually constructing a pullulanase variant to achieve any of the above objectives, it may be convenient to evaluate whether or not the contemplated amino acid modification can be accommodated into pullulanase structure, e.g. in a model of the three-dimensional structure of the parent pullulanase.

Pullulanase Variants with an Altered Substrate Specificity

One aim of the present invention is to change the degradation characteristics of a pullulanase. Thus, as Promozyme® (and pullulanases in general) exhibits a low activity towards high molecular weight branched starchy material, such as glycogen and amylopectin, it may be desirable to change this cleavage pattern, e.g. so as to obtain a higher activity against such substrates, in particular when the pullulanase is to be added during the liquefaction process.

An altered substrate specificity may be achieved by modifying the substrate binding area in a parent pullulanse.

Accordingly, the present invention also relates to a method for constructing a variant of a parent pullulanase, the method comprising:

a) identifying the substrate binding area in a model of the three-dimensional structure of the parent pullulanase;

b) modifying the substrate binding area by an amino acid substitution, deletion and/or insertion;

c) optionally repeating step b) recursively;

d) optionally, making alterations each of which is an insertion, a deletion or a substitution of an amino acid residue at one or more positions other than b), e) preparing the variant resulting from steps a)–d);

f) testing the substrate specificity of the variant;

g) optionally repeating steps a)–f) recursively; and h) selecting a variant having an altered substrate specificity as compared to the parent pullulanase.

The substrate binding area may easily be identified by homology to other family 13 members. The active site residues are identified by homology. The substrate-binding site is identified by the concave cavity containing the active site residues. A substrate model is docked into the cavity. A suitable substrate model is the substrate structure found in the pdb file 1BAG termed GLC. This model can be "docked" into the Promozyme X-ray structure or a modeled Pullulanase 3D structure by superimposing the active site residues in the two structures. In 1BAG one of the active site residues has been mutated into an Gln instead of the native Glu. The active site residues to be superimposed are: D269, Q208 and D176 (1BAG) with D736, E651 and D622 (Promozyme®). The superposition can be made using the program INSIGHTII.

Without being limited to any theory, it is presently believed that binding between a substrate and an enzyme is supported by favorable interactions found within a sphere 10 Å from the substrate molecule, in particular within a sphere of 6 Å from the substrate molecule. Examples of such favorable bonds are hydrogen bonds, strong electrostatic interaction and/or hydrophobic interactions. The following residues of Promozyme® (SEQ ID NO: 1), are within a distance of 10 Å from the "docked" substrate and thus believed to be involved in interactions with said substrate:

437, 439, 487, 489, 490, 514, 679, 681, 684, 685, 731, 775, 786,

494–496 (i.e. 494, 495 and 496),

505–511 (i.e. 505, 506, 507, 508, 509, 510 and 511),

551–559 (i.e. 551, 552, 553, 554, 555, 556, 557, 558 and 559),

584–590 (i.e. 584, 585, 586, 587, 588, 589 and 590),

620–626 (i.e. 620, 621, 622, 623, 624, 625, 626),

650–658 (i.e. 659, 651, 652, 653, 654, 655, 656, 657 and 568),

665–668 (i.e. 666, 667 and 668),

690–693 (i.e. 690, 691, 692 and 693),

734–738 (i.e. 734, 735, 736, 737 and 738) and

789–795 (i.e. 789, 790, 791, 792, 793, 794 and 795).

The following residues of Promozyme® are within a distance of 6 Å from the substrate and thus believed to be involved in interactions with said substrate:

489, 551, 553, 555, 556, 620, 651, 691, 692, 791, 793, 794,

506–510 (i.e. 507, 508, 509 and 510),

586–588 (i.e. 586, 587 and 588),

622–624 (i.e. 622, 623 and 624),

653–656 (i.e. 653, 654, 655 and 656) and

735–737 (i.e. 735, 736 and 737),

In a preferred embodiment of the invention, the parent pullulanase is modified in such a way that the variant pulluanase exhibits an increased isoamylase activity compared to the parent pullulanase.

When used herein, the term "increased isoamylase activity" refers in general to the fact that the pullulanase variants according to the invention exhibits a higher activity towards high molecular weight branched starchy material, such as glycogen and amylopectin as compared to the parent pullulanase, cf. above.

In an interesting embodiment of the invention the pullulanase variant has an increased isoamylase activity as defined by an increase of at least 5%, preferably of at least 10%, more preferably of at least 15%, more preferably of at least 25%, most preferably of at least 50%, in particular of at least 75%, such as of at least 100% in the number of reducing ends formed in the "assay for isoamylase-like activity" described herein, using 50 mM sodium acetate, a pH of 4.5, 5.0 or 5.5, a temperature of 60° C. and when incubated with a 10 w/v rabbit liver glycogen solution for a period of 10 min.

Similar modifications may be introduced in equivalent positions of other pullulanases. Substitutions of particular interest are any combination of one or both of the above with any of the other modifications disclosed herein.

For example, the following residues of the pullulanase from *Bacillus deramificans* (SEQ ID NO: 3) are within a distance of 10 Å from the "docked" substrate and thus believed to be involved in interactions with said substrate:

435, 437, 485, 487, 488, 512, 677, 679, 682, 683, 729, 773, 784,

492–494 (i.e. 492, 493 and 494),

503–509 (i.e. 503, 504, 505, 506, 507, 508 and 509),

549–557 (i.e. 549, 550, 551, 552, 553, 554, 555, 556 and 557),

582–588 (i.e. 582, 583, 584, 585, 586, 587 and 588),

618–624 (i.e. 618, 619, 620, 621, 622, 623 and 624),

648–656 (648, 649, 650, 651, 652, 653, 654, 655 and 656),

663–666 (i.e. 663, 664, 665 and 666),

688–691 (i.e. 688, 689, 690 and 691),

732–736 (732, 733, 734, 735 and 736) and

787–793 (i.e. 787, 788, 879, 790, 791, 792 and 793).

The following residues of the pullulanase from *Bacillus deramificans* (SEQ ID NO: 3) are within a distance of 6 Å from the substrate and thus believed to be involved in interactions with said substrate:

487, 549, 551, 553, 554, 618, 649, 689, 690, 789, 791, 792,

504–508 (i.e. 504, 505, 506, 507 and 508),

584–586 (i.e. 584, 585 and 586),

620–622 (i.e. 620, 621 and 622),

651–654 (i.e. 651, 652, 653 and 654) and

733–735 (i.e. 733, 734 and 735).

Examples of specific modifications in the above-mentioned regions of *Bacillus deramificans* are: L621I/V, D508M/N/L/T/V, T586I/L/V, T677W/F/Y, Y729F/I/L, D679G/A/V, S732V/T/L/I, N735G/L/V/I/S/T/A and Δ(688–691).

Pullulanase Variants with Altered pH Dependent Activity Profile

The pH dependent activity profile can be changed by changing the pKa of residues within 15 Å, in particular by changing the pKa of residues within 10 Å, from the active site residues of the parent pullulanase. Changing the pKa of the active site residues is achieved, e.g., by changing the electrostatic interaction or hydrophobic interaction between functional groups of amino acid side chains of a given amino acid residue and its close surroundings. To obtain a higher activity at a higher pH, negatively charged residues are placed near a hydrogen donor acid, whereas positively charged residues placed near a nucleophilic acid will result in higher activity at low pH. Also, a decrease in the pKa can be obtained by reducing the accessibility of water or increasing hydrophobicity of the environment.

It is preferred that the variant in question exhibits a pH optimum which is at least about 0.5 pH units higher or lower, preferably at least about 1.0 pH units higher or lower, than the corresponding pH optimum of the parent pullulanase when tested on a suitable substrate (e.g. pullulan, amylopectin or glycogen).

Furthermore, it is particular preferred that the variant in question exhibits an increased activity in the pH range of from 4 to 5.5 as compared to the parent pullulanase when tested on a suitable substrate (e.g. pullulan, amylopectin or glycogen).

Thus, another aspect of the present invention relates to a method for constructing a variant of a parent pullulanase, the method comprising:

a) identifying an amino acid residue which is within 15 Å, in particular within 10 Å, from an active site residue of the parent pullulanase in the three-dimensional structure of said parent pullulanse, and which is involved in electrostatic or hydrophobic interactions with an active site residue;

b) substituting said amino acid residue with another amino acid residue which changes the electrostatic and/or hydrophobic surroundings of an active site residue, and which can be accommodated in the structure;

c) optionally repeating steps a) and b) recursively;

d) optionally, making alterations each of which is an insertion, a deletion or a substitution of an amino acid residue at one or more positions other than b);

e) preparing the variant resulting from steps a)–d);

f) testing the pH dependent activity of said variant; and g) optionally repeating steps a)–f) recursively; and h) selecting a variant having an altered pH dependent activity as compared to the parent amylase.

In general, an amino acid residue which is within 15 Å or 10 Å, respectively, from an active site residue of the parent pullulanase may be identified by using the INSIGHTII program.

In a preferred embodiment, the variant of a parent pullulanase having an altered pH dependent activity profile as compared to the parent pullulanase comprises a modification, e.g. a substitution, of an amino acid residue corresponding to one or more of the following residues of the amino acid sequence set forth in SEQ ID NO: 1 (all within 15 Å from the active site residues D736, E651, D622):

430, 433, 518, 521, 565, 599, 600, 610, 611, 635, 636, 639, 717, 760, 763, 764, 767, 817,

435–443 (i.e. 435, 436, 437, 438, 439, 440, 441, 442, and 443),

486–496 (i.e. 486, 487, 488, 489, 490, 491, 492, 493, 494, 495 and 496),

505–515 (i.e. 505, 506, 507, 508, 509, 510, 511, 512, 513, 514 and 515),

548–560 (i.e. 548, 549, 550, 551, 552, 553, 554, 555, 556, 657, 558, 559 and 560), 573–575, (i.e. 573, 574 and 575), 583–595 (i.e. 583, 584, 585, 586, 587, 588, 589, 590, 591, 592, 593, 594 and 594), 602–604 (i.e. 602, 603 and 604), 606–608 (i.e. 606–607 and 608), 616–633 (i.e. 616, 617, 618, 619, 620, 621, 622, 623, 624, 625, 626, 627, 628, 629, 630, 631, 632, and 633), 646–672 (i.e. 646, 647, 648, 649, 650, 651, 652, 653, 654, 655, 656, 657, 658, 659, 660, 661, 662, 663, 664, 665, 666, 667, 668, 669, 670, 671 and 672), 674–696 (i.e. 674, 675, 676, 677, 678, 679, 680, 681, 682, 683, 684, 685, 686, 687, 688, 689, 690, 691, 692, 693, 694, 695 and 696), 720–722 (i.e. 720, 721 and 722), 725–747 (i.e. 725, 726, 727, 728, 729, 730, 731, 732, 733, 734, 735, 736, 737, 738, 739, 740, 741, 742, 743, 744, 745, 746 and 747), 773–781 (i.e. 773, 774, 775, 776, 777, 778, 779, 780 and 781), 783–797 (i.e. 783, 784, 785, 786, 787, 788, 789, 790, 791, 792, 793, 794, 795, 796 and 797) and 799–802 (i.e. 799, 800, 801 and 802).

Within 10 Å from the active site residues D736, E651, D622:

437, 442, 492, 514, 575, 594, 603, 632, 635, 684, 688, 691, 692, 721, 727, 729, 742, 743, 775, 777, 778, 780, 784, 786, 800,

487–490 (i.e. 487, 488, 489 and 490),

507–511 (i.e. 507, 508, 509, 510 and 511),

550–557 (i.e. 550, 551, 552, 553, 554, 555, 556 and 556),

585–588 (i.e. 585, 586, 587 and 588),

590–592 (i.e. 590, 591 and 592),

619–628 (i.e. 619, 620, 621, 622, 623, 624, 625, 626, 627 and 628),

648–655 (i.e. 648, 649, 650, 651, 652, 653, 654 and 655),

665–671 (i.e. 665, 666, 667, 668, 669, 670 and 671),

676–681 (i.e. 676, 677, 678, 679, 680 and 681),

731–740 (i.e. 731, 732, 733, 734, 735, 736, 737, 738, 739 and 740) and

788–793 (i.e. 788, 789, 790, 791, 792 and 793).

Similar modifications may be introduced in equivalent positions of other pullulanases. Variants of particular interest have a combination of one or more of the above with any of the other modifications disclosed herein.

Thus, in another preferred embodiment, the variant of a parent pullulanase having an altered pH dependent activity profile as compared to the parent pullulanase comprises a modification, e.g. a substitution, of an amino acid residue corresponding to one or more of the following residues. of the amino acid sequence set forth in SEQ ID NO: 3 (all within 15 Å from the active site residues D734, E649 and D620):

428, 431, 516, 519, 563, 597, 598, 608, 609, 633, 634, 637, 715, 758, 761, 762, 765, 815,

433–441 (i.e. 433, 434, 435, 436, 437, 438, 439, 440 and 441),

484–494 (i.e. 484, 485, 486, 487, 488, 489, 490, 491, 492, 493 and 494),

503–513 (i.e. 503, 504, 505, 506, 507, 508, 509, 510, 511, 512 and 513),

546–558 (546, 547, 548, 549, 550, 551, 552, 553, 554, 555, 556, 557 and 558),

571–573 (i.e. 571, 572 and 573),

581–593 (i.e. 581, 582, 583, 584, 585, 586, 587, 588, 589, 590, 591, 592 and 593), 600–602 (i.e. 600, 601 and 602), 604–606 (i.e. 604, 605 and 606), 614–631 (i.e. 614, 615, 616, 617, 618, 619, 620, 621, 622, 623, 624, 625, 626, 627, 628, 629, 630 and 631), 644–670 (i.e. 644, 645, 646, 647, 648, 649, 650, 651, 652, 653, 654, 655, 656, 657, 658, 659, 660, 661, 662, 663, 664, 665, 666, 667, 668, 669 and 670), 672–694 (i.e. 672, 673, 674, 675, 676, 677, 678, 679, 680, 681, 682, 683, 684, 685, 686, 687, 688, 689, 690, 691, 692, 693 and 694), 718–720 (i.e. 718, 719 and 720), 723–745 (i.e. 723, 734, 725, 726, 727, 728, 729, 730, 731, 732, 733, 734, 735, 736, 737, 738, 739, 740, 741, 742, 743, 744 and 745), 771–779 (i.e. 771, 772, 773, 774, 775, 776, 777, 778 and 779), 781–795 (i.e. 781, 782, 783, 784, 785, 786, 787, 788, 789, 790, 791, 792, 793, 794 and 795) and 797–800 (i.e. 797, 798, 799 and 800).

Within 10 Å from the active site residues D734, E649 and D620:

435, 440, 490, 512, 573, 601, 605, 630, 669, 682, 686, 689, 690, 719, 725, 727, 740, 741, 773, 775, 776, 778, 782, 784, 798,

485–488 (i.e. 485, 486, 487 and 488),

505–509 (i.e. 505, 506, 507, 508 and 509),

548–555 (i.e. 548, 549, 550, 551, 552, 553, 554 and 555),

583–586 (i.e. 583, 584, 585 and 586),

588–590 (i.e. 588, 589 and 590),

617–626 (i.e. 616, 617, 618, 619, 620, 621, 622, 623, 624, 625 and 626),

646–653 (i.e. 646, 647, 648, 649, 650, 651, 652 and 653),

663–667 (i.e. 663, 664, 665, 666 and 667),

674–679 (i.e. 674, 675, 676, 677, 678 and 679),

729–738 (i.e. 729, 730, 731, 732, 733, 734, 735, 736, 737 and 738) and

786–791 (i.e. 786, 787, 788, 789, 790 and 791).

Specific examples of substitutions in the above-mentioned positions include D437L/I/V/F, D440L/I/V/F, M486K, M487K, D503L/I/V/F, D508N/L/T/V, T586V/I, M630H and D437L/I/V/F+D440L/I/V/F+D503L/I/V/F.

Nomenclature for Amino Acid Modifications

The nomenclature used herein for defining modifications is essentially as described in WO 92/05249. Thus, G406A indicates a substitution of the amino acid G (Gly) in position 406 with the amino acid A (Ala). G406 indicates a substitution of the amino acid G (Gly) with any other amino acid. P394F/W/I/L indicates a substitution of P394 with F, W, I or L. Δ(688–691) indicates a deletion of amino acids in positions 688–691. 412-A-413 indicates an insertion of A between amino acids 412 and 413.

When used herein, the term "modification" (of a particular amino acid residue) is intended to cover substitution and deletion (of the particular amino acid residue) as well as insertion of one or more amino acid residues after the particular amino acid residue.

Polypeptide Sequence Homology

For purposes of the present invention, the degree of homology may be suitably determined according to the method described in S. B. Needleman and C. D. Wunsch, *Journal of Molecular Biology*, 48, 443–45, with the following settings for polypeptide sequence comparison: GAP creation penalty of 3.0 and GAP extension penalty of 0.1. The determination may be done by means of a computer program known such as GAP provided in the UWGCG program package (Program Manual for the Wisconsin Package, Version 8, August 1994, Genetics Computer Group, 575 Science Drive, Madison, Wis., USA 53711).

Hybridization

Suitable experimental conditions for determining hybridization between a nucleotide probe and a homologous DNA or RNA sequence involves presoaking of the filter containing the DNA fragments or RNA to hybridize in 5×SSC (sodium chloride/sodium citrate, Sambrook, et al. Molecular Cloning: A Laboratory Manual, $2^{nd}$ Ed., Cold Spring Harbor, 1989) for 10 min, and prehybridization of the filter in a solution of 5×SSC, 5×Denhardt's solution (Sambrook, et al., 1989), 0.5% SDS and 100 $\mu$g/ml of denatured sonicated salmon sperm DNA (Sambrook, et al., 1989), followed by hybridization in the same solution containing a random-primed (A. P. Feinberg B. and Vogelstein, *Anal. Biochem.* 132, 6–13 (1983)), $^{32}$P-dCTP-labeled (specific activity >1×10$^9$ cpm/$\mu$g) probe for 12 hours at ca. 45° C. The filter is then washed twice for 30 minutes in 2×SSC, 0.5% SDS at least 55° C. (low stringency), preferably at least 60° C. (medium stringency), more preferably at least 65° C. (medium/high stringency), more preferably at least 70° C. (high stringency), even more preferably at least 75° C. (very high stringency).

Molecules which hybridize to the oligonucleotide probe under these conditions are detected by exposure to x-ray film.

Methods of Preparing Pullulanase Variants According to the Invention

Cloning a DNA Sequence Encoding a Pullulanase

The DNA sequence encoding a parent pullulanase may be isolated from any cell or microorganism producing the pullulanase in question, using various methods well known in the art.

First, a genomic DNA and/or cDNA library should be constructed using chromosomal DNA or messenger RNA from the organism that produces the pullulanase to be studied. Then, if the amino acid sequence of the pullulanase is known, homologous, labelled oligonucleotide probes may be synthesised and used to identify pullulanase-encoding clones from a genomic library prepared from the organism in question. Alter-natively, a labelled oligonucleotide probe containing sequences homologous to a known pullulanase gene could be used as a probe to identify pullulanase-encoding clones, using hybridization and washing conditions of lower stringency.

Alternatively, the DNA sequence encoding the enzyme may be prepared synthetically by established standard methods, e.g. the phosphoroamidite method described by S. L. Beaucage and M. H. Caruthers, *Tetrahedron Letters*, 22, 1859–1869 (1981) or the method described by Matthes et al. *The EMBO*, 3, 801–805 (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin, wherein the fragments correspond to various parts of the entire DNA sequence, in accordance with techniques well known in the art. The DNA sequence may also be prepared by polymerase chain reaction (PCR) using specific primers, for instance as described in U.S. Pat. No. 4,683,202 or R. K. Saiki et al. *Science*, 239, 487–491(1988).

Site-directed Mutagenesis

Once a pullulanase-encoding DNA sequence has been isolated, and desirable sites for modification identified, modifications may be introduced using synthetic oligonucleotides. These oligonucleotides contain nucleotide sequences flanking the desired modification sites; mutant nucleotides are inserted during oligonucleotide synthesis. In a specific method, a single-stranded gap of DNA, bridging the pullulanase-encoding sequence, is created in a vector carrying the pullulanase gene. Then the synthetic nucleotide, bearing the desired modification, is annealed to a homologous portion of the single-stranded DNA. The remaining gap is then filled in with DNA polymerase I (Klenow fragment) and the construct is ligated using T4 ligase. A specific example of this method is described in Morinaga et al. *Biotechnology* 2, 639–646 (1984). U.S. Pat. No. 4,760,025 discloses the introduction of oligonucleotides encoding multiple modifications by performing minor alterations of the cassette. However, an even greater variety of modifications can be introduced at any one time by the Morinaga method because a multitude of oligonucleotides, of various lengths, can be introduced.

Another method of introducing modifications into a pullulanase-encoding DNA sequences is described in Nelson and Long *Analytical Biochemistry*, 180, 147–151 (1989). It involves a 3-step generation of a PCR fragment containing the desired modification introduced by using a chemically synthesized DNA strand as one of the primers in the PCR reactions. From the PCR-generated fragment, a DNA fragment carrying the modification may be isolated by cleavage with restriction endonucleases and reinserted into an expression plasmid.

Random Mutagenesis

Random mutagenesis is suitably performed either as localized or region-specific random mutagenesis in at least three parts of the gene translating to the amino acid sequence shown in question, or within the whole gene.

The random mutagenesis of a DNA sequence encoding a parent pullulanase may be conveniently performed by use of any method known in the art.

In relation to the above, a further aspect of the present invention relates to a method for generating a variant of a parent pullulanase, wherein the variant exhibits an altered property, such as increased thermostability, increased stability at low pH and at low calcium concentration, relative to the parent pullulanase, the method comprising:
(a) subjecting a DNA sequence encoding the parent pullulanase to random mutagenesis,
(b) expressing the mutated DNA sequence obtained in step (a) in a host cell, and
(c) screening for host cells expressing a pullulanase variant which has an altered property relative to the parent pullulanase.

Step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nudeobdes during the synthesis of the oligonucleotide at the positions which are to be changed. The doping or spiking may be done so that codons for unwanted amino acids are avoided. The doped or spiked oligonucleotide can be incorporated into the DNA encoding the pullulaase enzyme by any published technique, using e.g. PCR, LCR or any DNA polymerase and ligase as deemed appropriate.

Preferably, the doping is carried out using "constant random doping", in which the percentage of wild-type and modification in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% modifications in each position. An additional consideration in the choice of a doping scheme is based on genetic as well as protein-structural constraints. The doping scheme may be made by using the DOPE program which, inter alia, ensures that introduction of stop codons is avoided (L. J. Jensen et al. *Nucleic Acid Research*, 26, 697–702 (1998).

When PCR-generated mutagenesis is used, either a chemically treated or non-treated gene encoding a parent pullulanase enzyme is subjected to PCR under conditions that increase the misincorporation of nucleotides (Deshler 1992; Leung et al., *Technique*, 1, 1989, pp. 11–15).

A mutator strain of *E. coil* (Fowler et al., *Molec. Gen. Genet.*, 133, 1974, 179–191), *S. cereviseae* or any other microbial organism may be used for the random mutagenesis of the DNA encoding the pullulanase by, e.g., transforming a plasmid containing the parent enzyme into the mutator strain, growing the mutator strain with the plasmid and isolating the mutated plasmid from the mutator strain. The mutated plasmid may be subsequently transformed into the expression organism.

The DNA sequence to be mutagenized may conveniently be present in a genomic or cDNA library prepared from an organism expressing the parent pullulanase. Alternatively, the DNA sequence may be present on a suitable vector such as a plasmid or a bacteriophage, which as such may be incubated with or otherwise exposed to the mutagenising agent. The DNA to be mutagenized may also be present in a host cell either by being integrated in the genome of said cell or by being present on a vector harbored in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubaton with or exposure to the mutagenising agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, Streptomyces lividans* or *Streptomyces murinus*; and gram negative bacteria such as *E. coli*.

The mutated DNA sequence may further comprise a DNA sequence encoding functions permitting expression of the mutated DNA sequence.

Localized Random Mutagenesis

The random mutagenesis may be advantageously localized to a part of the parent pullulanase in question. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized, or region-specific, random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

General Method for Random Mutagenesis by Use of the DOPE Groaram

The random mutagenesis may be carried out by the following steps:
1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally reasonable mutations
5. Adjust the residues selected by step 3 with regard to step 4.
6. Analyze by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting pullulanase variants by screening for the desired improved properties.

Suitable dope algorithms for use in step 6 are well known in the art. One such algorithm is described by Tomandl, D. et al., 1997, Journal of Computer-Aided Molecular Design 11:29–38. Another algorithm is DOPE (Jensen, L J, Andersen, K V, Svendsen, A, and Kretzschmar, T (1998) Nucleic Acids Research 26:697–702).

Expression of Pullulanase Variants

The construction of the variant of interest is accomplished by cultivating a microorganism comprising a DNA sequence encoding the variant under conditions which are conducive for producing the variant, and optionally subsequently recovering the variant from the resulting culture broth. This is described in detail further below.

According to the invention, a DNA sequence encoding the variant produced by methods described above, or by any alternative methods known in the art, can be expressed, in the form of a protein or polypeptide, using an expression vector which typically includes control sequences encoding a promoter, operator, ribosome binding site, translation initiation signal, and, optionally, a repressor gene or various activator genes.

The recombinant expression vector carrying the DNA sequence encoding an pullulanase variant of the invention may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid, a bacteriophage or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA sequence encoding a pullulanase variant of the invention, especially in a bacterial host, are the promoter of the lac operon of E.coli, the Streptomyces coelicolor agarase gene dagA promoters, the promoters of the Bacillus licheniformis α-amylase gene (amyL), the promoters of the Bacillus stearothermophilus maltogenic amylase gene (amyM), the promoters of the Bacillus amyloliquefaciens α-amylase (amyQ), the promoters of the Bacillus subtilis xylA and xylB genes, etc. For transcription in a fungal host, examples of useful promoters are those derived from the gene encoding A. oryzae TAKA amylase, Rhizomucor miehei aspartic proteinase, A. niger neutral α-amylase, A. niger acid stable α-amylase, A. niger glucoamylase, Rhizomucor miehei lipase, A. oryzae alkaline protease, A. oryzae triose phosphate isomerase or A. nidulans acetamidase.

The expression vector of the invention may also comprise a suitable transcription terminator and, in eukaryotes, polyadenylation sequences operably connected to the DNA sequence encoding the pullulanase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from B. subtilis or B. licheniformis, or one which confers antibiotic resistance such as ampicillin, kanamycin, chloramphenicol or tetracycline resistance. Furthermore, the vector may comprise Aspergillus selection markers such as amdS, argB, niaD and sC, a marker giving rise to hygromycin resistance, or the selection may be accomplished by co-transformation, e.g. as described in WO 91/17243.

While intracellular expression may be advantageous in some respects, e.g. when using certain bacteria as host cells, it is generally preferred that the expression is extracellular. In general, the Bacillus α-amylases mentioned herein comprise a preregion permitting secretion of the expressed protease into the culture medium. If desirable, this preregion may be replaced by a different preregion or signal sequence, conveniently accomplished by substitution of the DNA sequences encoding the respective preregions.

The procedures used to ligate the DNA construct of the invention encoding the pullulanase variant, the promoter, terminator and other elements, respectively, and to insert them into suitable vectors containing the information necessary for replication, are well known to persons skilled in the art (cf., for instance, Sambrook et al. Molecular Cloning: A Laboratory Manual, $2^{nd}$ Ed., Cold Spring Harbor, 1989).

The cell of the invention, either comprising a DNA construct or an expression vector of the invention as defined above, is advantageously used as a host cell in the recombinant production of a pullulanase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but is preferably a microbial cell, e.g. a bacterial or a fungal (including yeast) cell.

Examples of suitable bacteria are gram positive bacteria such as Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis, or Streptomyces lividans or Streptomyces murinus, or gram negative bacteria such as E.coli. The transformation of the bacteria may, for instance, be effected by protoplast transformation or by using competent cells in a manner known per se.

The yeast organism may favourably be selected from a species of Saccharomyces or Schizosaccharomyces, erg. Saccharomyces cerevisiae. The filamentous fungus may advantageously belong to a species of Aspergillus, e.g. Aspergillus oryzae or Aspergillus niger. Fungal cells may be transformed by a process involving protoplast formation and transformation of the protoplasts followed by regeneration of the cell wall in a manner known per se. A suitable procedure for transformation of Aspergillus host cells is described in EP 238 023.

In a yet further aspect, the present invention relates to a method for producing a pullulanase variant of the invention, the method comprising: cultivating a host cell as described above under conditions conducive to the production of the variant and recovering the variant from the cells and/or culture medium.

The medium used to cultivate the cells may be any conventional medium suitable for growing the host cell in question and obtaining expression of the pullulanase variant of the invention. Suitable media are available from commercial suppliers or may be prepared according to published recipes (e.g. as described in catalogues of the American Type Culture Collection).

The pullulanase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Testing of Pullulanase

Pullulanase variants produced by any of the methods described above may be tested, either prior to or after purification, for pullulanase activity in a screening assay which measures the ability of the variant to degrade pullulan or, in case it is desired to screen for an increased isoamylases activity, the ability of the variant to degrade amylopectin. The screening in step 10 in the above-mentioned random mutagenesis method of the invention may be conveniently performed by use of a filter assay based on the following procedure: A microorganism capable of expressing the mutated pullulanase of interest is incubated on a suitable medium and under suitable conditions for secretion of the enzyme, the medium being covered with two filters comprising a protein-binding filter placed under a second filter exhibiting a low protein binding capability. The microorganism is grown on the second, top filter. Subsequent to the incubation, the bottom protein-binding filter comprising enzymes secreted from the microorganism is separated from the second filter comprising the microorganism. The protein-binding filter is then subjected to screening for the desired enzymatic activity, and the corresponding microbial colonies present on the second filter are identified. The first filter used for binding the enzymatic activity may be any protein-binding filter, e.g., nylon or nitrocellulose. The second filter carrying the colonies of the expression organism may be any filter that has no or low affinity for binding proteins, e.g., cellulose acetate or Durapore™.

Screening consists of treating the first filter to which the secreted protein is bound with a substrate that allows detection of the activity. The enzymatic activity may be detected by a dye, fluorescence, precipitation, pH indicator, IR-absorbance or any other known technique for detection of enzymatic activity. The detecting compound may be immobilized by any immobilizing agent e.g. agarose, agar, gelatine, polyacrylamide, starch, filter paper, cloth; or any combination of immobilizing agents. For example, isoamylase activity can be detected by Cibacron Red labelled amylopectin, which is immobilized in agarose. isoamylase activity on this substrate produces zones on the plate with reduced red color intensity (clearing zones).

To screen for variants with increased stability, the filter with bound pullulanase variants can be pretreated prior to the detection step described above to inactivate variants that do not have improved stability relative to the parent pullulanase. This inactivation step may consist of, but is not limited to, incubation at elevated temperatures in the presence of a buffered solution at any pH from pH 2 to 12, and/or in a buffer containing another compound known or thought to contribute to altered stability e.g., surfactants, EDTA, EGTA, wheat flour components, or any other relevant additives. Filters so treated for a specified time are then rinsed briefly in deionized water and placed on plates for activity detection as described above. The conditions are chosen such that stabilized variants show increased enzymatic activity relative to the parent after incubation on the detection media.

To screen for variants with altered thermostability, filters with bound variants are incubated in buffer at a given pH (e.g., in the range from pH 2–12) at an elevated temperature (e.g., in the range from 50°–110° C.) for a time period (e.g., from 1–20 minutes) to inactivate nearly all of the parent pullulanase, rinsed in water, then placed directly on a detection plate containing immobilized Cibacron Blue labeled pullulan and incubated until activity is detectable. As will be understood, thermostability and increased isoamylase activity may be tested simultaneously by using a detection plate containing immobilized Cibacron Red labeled amylopectin and incubate until activity is detectable. Moreover, pH dependent stability can be screened for by adjusting the pH of the buffer in the above inactivation step such that the parent pullulanase is inactivated, thereby allowing detection of only those variants with increased stability at the pH in question. To screen for variants with increased calcium-dependent stability, calcium chelators, such as ethylene glycol-bis(β-aminoethyl ether) N,N,N',N'-tetraacetic acid (EGTA), is added to the inactivation buffer at a concentration such that the parent pullulanase is inactivated under conditions further defined, such as buffer pH, temperature or a specified length of incubation.

The variants of the invention may be suitably tested by assaying the pullulan- or amylopectin-degrading activity of the variant, for instance by growing host cells transformed with a DNA sequence encoding a variant on a starch-containing agarose plate and identifying pullulan- and/or amylopectin-degrading host cells as described above. Further testing in regard to altered properties, including specific activity, substrate specificity, cleavage pattern, thermoactivation, thermostability, pH dependent activity or optimum, pH dependent stability, temperature dependent activity or optimum, transglycosylation activity, stability, and any other parameter of interest, may be performed on purified variants in accordance with methods known in the art as described below.

The invention is further illustrated with reference to the following examples which are not intended to be in any way limiting to the scope of the invention as claimed.

EXAMPLES

Determination of Pullulanase Activity

Endo-pullulanase activity in NPUN is measured relative to a Novo Nordisk pullulanase standard. One pullulanase unit (NPUN) is defined as the amount of enzyme which releases 1 mmol glucose per minute under the standard conditions (0.7% red pullulan, pH 5, 40° C., 20 minutes). The activity is measured in NPUN/ml using red pullulan. 1 ml diluted sample or standard is incubated at 40° C. for 2 minutes. 0.5 ml 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10–60 minutes followed by centrifugation 10 minutes at 4000 rpm. OD of the supernatants is then measured at 510 nm and the activity calculated using a standard curve.

Expression of Pullulanase from *Bacillus deramificans*

The pullulanase from *Bacillus deramificans* (SEQ ID NO: 3) is expressed in *B. subtilis* from a plasmid denoted pCA36. This plasmid contains the complete gene encoding the pullulanase, the expression of which is directed by the promoter from *Bacillus amyloliquefaciens* α-amylase. Further, the plasmid contains the origin of replication, oriT, from plasmid pUB110 and the cat gene from plasmid pC194 conferring resistance towards chloramphenicol. PCA36 is shown in FIG. 1.

Example 1

Construction of *Bacillus deramificans* D620A Variant

Gene specific primer 132011 and mutagenic primer 132012 are used to amplify by PCR an approximately 410 bp DNA fragment from the pCA36 plasmid.

The 410 bp fragment is purified from an agarose gel and used as a Mega-primer together with primer 136054 in a second PCR carried out on the same template.

The resulting approximately 1110 bp fragment is digested with restriction enzymes BsiW I and Mlu I and the resulting approximately 330 bp DNA fragment is purified and ligated with the pCA36 plasmid digested with the same enzymes. Competent *Bacillus subtilis* SHA273 (amylase and protease low) cells are transformed with the ligation and chloramphenicol resistant transformants are checked by colony PCR.

The mutagenesis primer 132012 introduced the D620A substitution (written in bold in the primer seq.) and introduced simultaneously a Bgl I restriction site (underlined in the primer seq.), which facilitates easy pinpointing of mutants.

Finally, DNA sequencing was carried out to verify the presence of the correct mutations on the plasmid.

Primer 132011:

5'CGCTTCGGAATCATTAGGATTGC 3' (SEQ ID NO:7)

Primer 132012:

5'GCTTCCGTTTTGCCTTAATGGCGCTGC 3' (SEQ ID NO:8)

Primer 136054:

5'GGCCAAGGCTCTACCCGAACGGC 3' (SEQ ID NO:9)

Example 2

Construction of *Bacillus deramificans* E649A Variant

This variant constructed as described in Example 1, except that mutagenic primer 132013 is used. The mutagenesis primer 132013 introduced the E649A substitution (written in bold in the primer seq.) and a Nar I restriction site(underlined in the primer seq.), which facilitates easy pinpointing of mutants.

Primer 132013:

5'GCACTTTACGGGGCGCCATGGACGGG 3' (SEQ ID NO:10)

What is claimed is:

1. A method for producing a variant of a parent pullulanase, wherein the parent pullulanase has more than 50% homology with the amino acid sequence shown in SEQ ID NO: 2, SEQ ID NO: 4 or SEQ ID NO:6, and wherein the variant has at least one altered property as compared to the parent pullulanase, the method comprising:

a) modeling the parent pullulanase on the three-dimensional structure of SEQ ID NO:2 depicted in Appendix 1 to produce a three-dimensional structure of the parent pullulanase;

b) identifying in the three-dimensional structure obtained in step (a) at least one structural part of the parent pullulanase, wherein an alteration in said structural part is predicted to result in an altered property;

c) modifying the nucleic acid sequence encoding the parent pullulanase to produce a nucleic add sequence encoding a variant of the parent pullulanase having a deletion, insertion, or substitution of one or more amino acids at a position corresponding to said structural part; and d) expressing the modified nucleic acid sequence in a host cell to produce the variant pullulanase.

2. The method of claim 1, wherein the altered property is pH dependent activity, thermostability, substrate cleavage pattern, specific activity of cleavage, substrate specificity or substrate binding.

3. The method of claim 2, wherein the altered property is a higher isoamylase activity as defined by an increase of at least 5% in the number of reducing ends formed in an "assay for isoamylase-like activity" using 50 mM sodium acetate, a pH of 4.5, 5.0 or 5.5 a temperature of 60° C. and when incubated with a 10% w/v rabbit liver glycogen solution for a period of 10 min.

4. The method of claim 1, wherein the altered property is an improved thermostability as defined by differential scanning calorimetry (DSC).

5. The method of claim 1, wherein the altered property is an improved thermostability es defined by an increased half-life ($T_{1/2}$) of at least about 5% in a "$T_{1/2}$ assay for liquefaction", using a pH of 5.0 and a temperature of 95° C.

6. The method of claim 1, wherein the altered property is an improved thermostability as defined by an increased residual enzyme activity of at least about 5% in an "assay for residual activity after liquefaction", using a pH of 5.0 and a temperature of 95° C.

7. The method of claim 1, wherein the altered property is an improved thermostability as defined by an increased half-life ($T_{1/2}$) of at least about 5%, in a "$T_{1/2}$ assay for saccharification", using a pH of 4.5 and a temperature of 70° C.

8. The method of claim 1, wherein the altered property is an improved thermostability as defined by an increased residual enzyme activity of at least about 5% in an "assay for residual activity after saccharification", using a pH of 4.5 and a temperature of 63° C.

9. The method according to claim 8, wherein the "assay for activity for saccharification", is carried out at a pH of 4.5 and at a temperature of 70° C.

10. A method according to claim 1, wherein the parent pullulanase has more than 60% homology with the amino acid sequence shown in SEQ ID NO: 2, SEQ ID NO: 4 or SEQ ID NO: 6.

11. A method according to claim 10, wherein the parent pullulanase has the amino acid sequences shown in SEQ ID NO: 2, SEQ ID NO: 4 or SEQ ID NO:6.

12. A method according to claim 1, wherein the parent pullulanase has more than 70% homology with the amino acid sequence shown in SEQ ID NO: 2, SEQ ID NO: 4 or SEQ ID NO: 6.

13. A method according to claim 1, wherein the parent pullulanase has more than 80% homology with the amino acid sequence shown in SEQ ID NO: 2, SEQ ID NO: 4 or SEQ ID NO: 6.

14. A method according to claim 1, wherein the parent pullulanase has more than 90% homology with the amino acid sequence shown in SEQ ID NO: 2, SEQ ID NO: 4 or SEQ ID NO: 6.

15. A method according to claim 1, wherein the parent pullulanase has more than 95% homology with the amino acid sequence shown in SEQ ID NO: 2, SEQ ID NO: 4 or SEQ ID NO: 6.

16. A method according to claim 1, wherein the parent pullulanase has more than 99% homology with the amino acid sequence shown in SEQ ID NO: 2, SEQ ID NO: 4 or SEQ ID NO: 6.

17. A method for constructing a variant of a parent pullulanase, wherein the parent pullulanase has more than 50% homology with the amino acid sequence shown in SEQ ID NO: 2, SEQ ID NO: 2 or SEQ ID NO:6, and wherein the variant has at least one altered property as compared to the parent pullulanase, the method comprising:

a) modeling the parent pullulanase on the three-dimensional structure of SEQ ID NO:2depicted in Appendix 1 to produce a three-dimensional structure of the parent pullulanase;

b) identifying an internal or external cavity or crevice in a three-dimensional structure of the parent pullulanase;

c) substituting at least one amino acid residue in the vicinity of the cavity or crevice with another amino acid residue which increases the hydrophobic interaction and/or fills out or reduces the size of the cavity or crevice;

d) preparing the variant resulting from steps b) and c);

e) testing the thermostability of the variant; and f) selecting a variant having increased thermostability as compared to the parent pullulanase.

18. A method according to claim 17, wherein the increased thermostability is as defined by differential scanning calorimetry.

19. A method for producing a pullulanase variant, the method comprising:

constructing the variant by the method according to claim 17, transforming a microorganism with a DNA sequence encoding the variant; and cultivating the transformed microorganism under conditions which are conducive for producing the variant.

20. The method of claim 19, wherein the method further comprises recovering the variant from the cultivation.

21. A method according to claim 17, wherein the parent pullulanase has more than 60% homology with the amino acid sequence shown in SEQ ID NO: 2, SEQ ID NO: 4 or SEQ ID NO: 6.

22. A method according to claim 17, wherein the parent pullulanase has more than 70% homology with the amino add sequence shown in SEQ ID NO: 2, SEQ ID NO: 4 or SEQ ID NO: 6.

23. A method according to claim 17, wherein the parent pullulanase has more than 80% homology with the amino acid sequence shown in SEQ ID NO: 2, SEQ ID NO: 4 or SEQ ID NO: 6.

24. A method according to claim 17, wherein the parent pullulanase has more than 90% homology with the amino acid sequence shown in SEQ ID NO: 2, SEQ ID NO: 4 or SEQ ID NO: 6.

25. A method according to claim 17, wherein the parent pullulanase has more than 95% homology with the amino acid sequence shown in SEQ ID NO: 2, SEQ ID NO: 4 or SEQ ID NO: 6.

26. A method according to claim 17, wherein the parent pullulanase has more than 99% homology with the amino add sequence shown in SEQ ID NO: 2, SEQ ID NO: 4 or SEQ ID NO: 6.

27. The method of claim 17, wherein said method comprises repeating steps b) and c) recursively.

* * * * *

SEQUENCE LISTING

<160> NUMBER OF SEQ ID NOS: 10

<210> SEQ ID NO 1
<211> LENGTH: 2766
<212> TYPE: DNA
<213> ORGANISM: Bacillus acidopullulyticus
<220> FEATURE:
<221> NAME/KEY: CDS
<222> LOCATION: (1)...(2763)

<400> SEQUENCE: 1

```
gat tct act tcg act aaa gtt att gtt cat tat cat cgt ttt gat tcc      48
Asp Ser Thr Ser Thr Lys Val Ile Val His Tyr His Arg Phe Asp Ser
 1               5                  10                  15 aac tat acg aat tgg gac gtc tgg atg tgg cct tat cag cct gtt aat      96
Asn Tyr Thr Asn Trp Asp Val Trp Met Trp Pro Tyr Gln Pro Val Asn
             20                  25                  30 ggt aat gga gca gct tac caa ttc act ggt aca aat gat gat ttt ggc     144
Gly Asn Gly Ala Ala Tyr Gln Phe Thr Gly Thr Asn Asp Asp Phe Gly
         35                  40                  45 gct gtt gca gat acg caa gtg cct gga gat aat aca caa gtt ggt ttg     192
Ala Val Ala Asp Thr Gln Val Pro Gly Asp Asn Thr Gln Val Gly Leu
     50                  55                  60 att gtt cgt aaa aat gat tgg agc gag aaa aat aca cca aac gat ctc     240
Ile Val Arg Lys Asn Asp Trp Ser Glu Lys Asn Thr Pro Asn Asp Leu
 65                  70                  75                  80 cat att gac ctt gca aaa ggc cat gaa gta tgg att gta caa ggg gat     288
His Ile Asp Leu Ala Lys Gly His Glu Val Trp Ile Val Gln Gly Asp
                 85                  90                  95 cca act att tat tac aat ctg agc gac gca cag gct gcc gca ata cca     336
Pro Thr Ile Tyr Tyr Asn Leu Ser Asp Ala Gln Ala Ala Ala Ile Pro
            100                 105                 110 tct gtt tca aat gcc tat ctt gat gat gaa aaa aca gta cta gca aag     384
Ser Val Ser Asn Ala Tyr Leu Asp Asp Glu Lys Thr Val Leu Ala Lys
        115                 120                 125 cta agt atg ccg atg acg ctg gcg gat gct gca agc ggc ttt acg gtt     432
Leu Ser Met Pro Met Thr Leu Ala Asp Ala Ala Ser Gly Phe Thr Val
    130                 135                 140 ata gat aaa acc aca ggt gaa aaa atc cct gtc acc tct gct gta tcc     480
Ile Asp Lys Thr Thr Gly Glu Lys Ile Pro Val Thr Ser Ala Val Ser
145                 150                 155                 160 gca aat ccg gta act gcc gtt ctt gtt gga gat tta caa cag gct ttg     528
Ala Asn Pro Val Thr Ala Val Leu Val Gly Asp Leu Gln Gln Ala Leu
                165                 170                 175 gga gca gcg aat aat tgg tca cca gat gat gat cac aca ctg cta aaa     576
Gly Ala Ala Asn Asn Trp Ser Pro Asp Asp Asp His Thr Leu Leu Lys
            180                 185                 190 aag ata aat cca aac ctt tac caa tta tcg ggg aca ctt cca gct ggt     624
Lys Ile Asn Pro Asn Leu Tyr Gln Leu Ser Gly Thr Leu Pro Ala Gly
```

```
            195                 200                 205
aca tac caa tat aag ata gcc ttg gac cat tct tgg aat acc tcc tat      672
Thr Tyr Gln Tyr Lys Ile Ala Leu Asp His Ser Trp Asn Thr Ser Tyr
    210                 215                 220 cca ggt aac aat gta agt ctt act gtt cct cag gga ggg gaa aag gtt      720
Pro Gly Asn Asn Val Ser Leu Thr Val Pro Gln Gly Gly Glu Lys Val
225                 230                 235                 240 acc ttt acc tat att cca tct acc aac cag gta ttc gat agc gtc aat      768
Thr Phe Thr Tyr Ile Pro Ser Thr Asn Gln Val Phe Asp Ser Val Asn
                245                 250                 255 cat cct aac caa gca ttc cct aca tcc tca gca ggg gtc cag aca aat      816
His Pro Asn Gln Ala Phe Pro Thr Ser Ser Ala Gly Val Gln Thr Asn
            260                 265                 270 tta gtc caa ttg act tta gcg agt gca ccg gat gtc acc cat aat tta      864
Leu Val Gln Leu Thr Leu Ala Ser Ala Pro Asp Val Thr His Asn Leu
        275                 280                 285 gat gta gca gca gac ggt tac aaa gcg cac aat att tta cca agg aat      912
Asp Val Ala Ala Asp Gly Tyr Lys Ala His Asn Ile Leu Pro Arg Asn
    290                 295                 300 gtt tta aat ctg ccg cgg tat gat tat agt gga aat gat ttg ggt aat      960
Val Leu Asn Leu Pro Arg Tyr Asp Tyr Ser Gly Asn Asp Leu Gly Asn
305                 310                 315                 320 gtt tat tca aag gat gca aca tcc ttc cgg gta tgg gct cca aca gct     1008
Val Tyr Ser Lys Asp Ala Thr Ser Phe Arg Val Trp Ala Pro Thr Ala
                325                 330                 335 tcg aat gtc cag ttg ctt tta tac aat agt gag aaa ggt tca ata act     1056
Ser Asn Val Gln Leu Leu Leu Tyr Asn Ser Glu Lys Gly Ser Ile Thr
            340                 345                 350 aaa cag ctt gaa atg caa aag agt gat aac ggt aca tgg aaa ctt cag     1104
Lys Gln Leu Glu Met Gln Lys Ser Asp Asn Gly Thr Trp Lys Leu Gln
        355                 360                 365 gtt tct ggt aat ctt gaa aac tgg tat tat cta tat caa gtc aca gtg     1152
Val Ser Gly Asn Leu Glu Asn Trp Tyr Tyr Leu Tyr Gln Val Thr Val
    370                 375                 380 aat ggg aca aca caa acg gca gtt gat cca tat gcg cgt gct att tct     1200
Asn Gly Thr Thr Gln Thr Ala Val Asp Pro Tyr Ala Arg Ala Ile Ser
385                 390                 395                 400 gtc aat gca aca cgc ggt atg att gtg gac cta aaa gct acc gat cct     1248
Val Asn Ala Thr Arg Gly Met Ile Val Asp Leu Lys Ala Thr Asp Pro
                405                 410                 415 gca ggg tgg cag gga gat cat gaa cag aca cct gcg aat cca gta gat     1296
Ala Gly Trp Gln Gly Asp His Glu Gln Thr Pro Ala Asn Pro Val Asp
            420                 425                 430 gaa gtg att tat gaa gcg cat gta cgc gat ttt tcg att gat gct aat     1344
Glu Val Ile Tyr Glu Ala His Val Arg Asp Phe Ser Ile Asp Ala Asn
        435                 440                 445 tca ggt atg aaa aat aaa ggg aag tat tta gcg ttt aca gag cat gga     1392
Ser Gly Met Lys Asn Lys Gly Lys Tyr Leu Ala Phe Thr Glu His Gly
    450                 455                 460 aca aaa gga ccg gat cat gta aag aca ggt att gat agt ttg aag gaa     1440
Thr Lys Gly Pro Asp His Val Lys Thr Gly Ile Asp Ser Leu Lys Glu
465                 470                 475                 480 ttg ggc atc acc act gtt caa ttg caa cct gtt gag gag ttt aac agt     1488
Leu Gly Ile Thr Thr Val Gln Leu Gln Pro Val Glu Glu Phe Asn Ser
                485                 490                 495 att gat gag acc cag cct gat acg tat aac tgg ggc tac gat cca agg     1536
Ile Asp Glu Thr Gln Pro Asp Thr Tyr Asn Trp Gly Tyr Asp Pro Arg
            500                 505                 510 aac tat aac gta cca gag gga gct tat gcc aca act cca gaa gga aca     1584
```

```
                                                                      -continued Asn Tyr Asn Val Pro Glu Gly Ala Tyr Ala Thr Thr Pro Glu Gly Thr
        515                 520                 525 gcg cgt ata aca gaa tta aag caa tta att caa agc ctt cat cag cag       1632
Ala Arg Ile Thr Glu Leu Lys Gln Leu Ile Gln Ser Leu His Gln Gln
530                 535                 540 cgg att ggt gtc aat atg gat gtt gtt tat aac cat acc ttt gat gtg       1680
Arg Ile Gly Val Asn Met Asp Val Val Tyr Asn His Thr Phe Asp Val
545                 550                 555                 560 atg gtt tct gat ttt gat aaa att gtc ccg caa tat tat cgt acc           1728
Met Val Ser Asp Phe Asp Lys Ile Val Pro Gln Tyr Tyr Arg Thr
                565                 570                 575 gat agt aat ggc aat tat acg aac gga tca ggt tgc ggc aat gaa ttc       1776
Asp Ser Asn Gly Asn Tyr Thr Asn Gly Ser Gly Cys Gly Asn Glu Phe
                580                 585                 590 gcg act gag cat cca atg gca caa aag ttt gtg ctt gat tca gtt aat       1824
Ala Thr Glu His Pro Met Ala Gln Lys Phe Val Leu Asp Ser Val Asn
            595                 600                 605 tat tgg gta aat gag tac cac gtg gat ggc ttc cgt ttt gac tta atg       1872
Tyr Trp Val Asn Glu Tyr His Val Asp Gly Phe Arg Phe Asp Leu Met
610                 615                 620 gct ctt tta gga aaa gac acg atg gca aaa ata tca aac gag ctg cat       1920
Ala Leu Leu Gly Lys Asp Thr Met Ala Lys Ile Ser Asn Glu Leu His
625                 630                 635                 640 gcc att aat cct ggt att gtt tta tat gga gaa cca tgg act ggc ggc       1968
Ala Ile Asn Pro Gly Ile Val Leu Tyr Gly Glu Pro Trp Thr Gly Gly
                645                 650                 655 aca tcg gga tta tct agc gac cag ctt gta acg aag ggt caa caa aag       2016
Thr Ser Gly Leu Ser Ser Asp Gln Leu Val Thr Lys Gly Gln Gln Lys
                660                 665                 670 gga tta gga att ggc gtt ttc aac gat aat ata cgt aat ggg ctc gat       2064
Gly Leu Gly Ile Gly Val Phe Asn Asp Asn Ile Arg Asn Gly Leu Asp
            675                 680                 685 ggg aac gtg ttt gat aaa acg gca caa ggc ttt gca aca gga gat cca       2112
Gly Asn Val Phe Asp Lys Thr Ala Gln Gly Phe Ala Thr Gly Asp Pro
690                 695                 700 aac cag gtg gat gtc att aaa aat gga gta atc ggt agt att caa gat       2160
Asn Gln Val Asp Val Ile Lys Asn Gly Val Ile Gly Ser Ile Gln Asp
705                 710                 715                 720 ttt act tca gca cct agc gaa acg att aac tat gtt aca agc cat gat       2208
Phe Thr Ser Ala Pro Ser Glu Thr Ile Asn Tyr Val Thr Ser His Asp
                725                 730                 735 aac atg acg ctt tgg gat aaa att tta gca agt aat cca agt gac act       2256
Asn Met Thr Leu Trp Asp Lys Ile Leu Ala Ser Asn Pro Ser Asp Thr
                740                 745                 750 gag gct gac cga att aaa atg gat gaa ttg gca cat gcc gta gta ttc       2304
Glu Ala Asp Arg Ile Lys Met Asp Glu Leu Ala His Ala Val Val Phe
            755                 760                 765 act tca caa ggt gta cca ttt atg caa ggt gga gaa gaa atg ctg agg       2352
Thr Ser Gln Gly Val Pro Phe Met Gln Gly Gly Glu Glu Met Leu Arg
770                 775                 780 aca aaa ggc gga aat gat aac agt tat aac gct gga gat agt gtg aat       2400
Thr Lys Gly Gly Asn Asp Asn Ser Tyr Asn Ala Gly Asp Ser Val Asn
785                 790                 795                 800 cag ttc gac tgg tca aga aag gcg caa ttt aag gat gtt ttt gac tac       2448
Gln Phe Asp Trp Ser Arg Lys Ala Gln Phe Lys Asp Val Phe Asp Tyr
                805                 810                 815 ttt tct agt atg att cat ctt cgt aat cag cac ccg gca ttc agg atg       2496
Phe Ser Ser Met Ile His Leu Arg Asn Gln His Pro Ala Phe Arg Met
                820                 825                 830
```

-continued

```
acg aca gcg gat caa att aaa cag aat ctt aca ttc tta gaa agc cca      2544
Thr Thr Ala Asp Gln Ile Lys Gln Asn Leu Thr Phe Leu Glu Ser Pro
            835                 840                 845 aca aac acg gta gct ttc gag tta aag aat tat gca aac cat gat aca      2592
Thr Asn Thr Val Ala Phe Glu Leu Lys Asn Tyr Ala Asn His Asp Thr
850                 855                 860 tgg aaa aat ata att gtc atg tat aac cca aat aag act tcc caa acc      2640
Trp Lys Asn Ile Ile Val Met Tyr Asn Pro Asn Lys Thr Ser Gln Thr
865                 870                 875                 880 ctt aat cta cca agt gga gat tgg acc att gta gga ttg gga gat caa      2688
Leu Asn Leu Pro Ser Gly Asp Trp Thr Ile Val Gly Leu Gly Asp Gln
                885                 890                 895 ata ggt gag aaa tca tta ggg cat gta atg ggt aat gtt caa gta ccg      2736
Ile Gly Glu Lys Ser Leu Gly His Val Met Gly Asn Val Gln Val Pro
            900                 905                 910 gct ata agt acg ctt att ctc aaa caa taa                              2766
Ala Ile Ser Thr Leu Ile Leu Lys Gln
            915                 920

<210> SEQ ID NO 2
<211> LENGTH: 921
<212> TYPE: PRT
<213> ORGANISM: Bacillus acidopullulyticus

<400> SEQUENCE: 2

Asp Ser Thr Ser Thr Lys Val Ile Val His Tyr His Arg Phe Asp Ser
1               5                   10                  15

Asn Tyr Thr Asn Trp Asp Val Trp Met Trp Pro Tyr Gln Pro Val Asn
            20                  25                  30

Gly Asn Gly Ala Ala Tyr Gln Phe Thr Gly Thr Asn Asp Asp Phe Gly
        35                  40                  45

Ala Val Ala Asp Thr Gln Val Pro Gly Asp Asn Thr Gln Val Gly Leu
    50                  55                  60

Ile Val Arg Lys Asn Asp Trp Ser Glu Lys Asn Thr Pro Asn Asp Leu
65                  70                  75                  80

His Ile Asp Leu Ala Lys Gly His Glu Val Trp Ile Val Gln Gly Asp
                85                  90                  95

Pro Thr Ile Tyr Tyr Asn Leu Ser Asp Ala Gln Ala Ala Ile Pro
            100                 105                 110

Ser Val Ser Asn Ala Tyr Leu Asp Asp Glu Lys Thr Val Leu Ala Lys
        115                 120                 125

Leu Ser Met Pro Met Thr Leu Ala Asp Ala Ser Gly Phe Thr Val
    130                 135                 140

Ile Asp Lys Thr Thr Gly Glu Lys Ile Pro Val Thr Ser Ala Val Ser
145                 150                 155                 160

Ala Asn Pro Val Thr Ala Val Leu Val Gly Asp Leu Gln Gln Ala Leu
                165                 170                 175

Gly Ala Ala Asn Asn Trp Ser Pro Asp Asp His Thr Leu Leu Lys
            180                 185                 190

Lys Ile Asn Pro Asn Leu Tyr Gln Leu Ser Gly Thr Leu Pro Ala Gly
        195                 200                 205

Thr Tyr Gln Tyr Lys Ile Ala Leu Asp His Ser Trp Asn Thr Ser Tyr
    210                 215                 220

Pro Gly Asn Asn Val Ser Leu Thr Val Pro Gln Gly Gly Glu Lys Val
225                 230                 235                 240

Thr Phe Thr Tyr Ile Pro Ser Thr Asn Gln Val Phe Asp Ser Val Asn
                245                 250                 255
```

-continued

```
His Pro Asn Gln Ala Phe Pro Thr Ser Ser Ala Gly Val Gln Thr Asn
            260                 265                 270

Leu Val Gln Leu Thr Leu Ala Ser Ala Pro Asp Val Thr His Asn Leu
        275                 280                 285

Asp Val Ala Ala Asp Gly Tyr Lys Ala His Asn Ile Leu Pro Arg Asn
        290                 295                 300

Val Leu Asn Leu Pro Arg Tyr Asp Tyr Ser Gly Asn Asp Leu Gly Asn
305                 310                 315                 320

Val Tyr Ser Lys Asp Ala Thr Ser Phe Arg Val Trp Ala Pro Thr Ala
                325                 330                 335

Ser Asn Val Gln Leu Leu Tyr Asn Ser Glu Lys Gly Ser Ile Thr
            340                 345                 350

Lys Gln Leu Glu Met Gln Lys Ser Asp Asn Gly Thr Trp Lys Leu Gln
        355                 360                 365

Val Ser Gly Asn Leu Glu Asn Trp Tyr Tyr Leu Tyr Gln Val Thr Val
        370                 375                 380

Asn Gly Thr Thr Gln Thr Ala Val Asp Pro Tyr Ala Arg Ala Ile Ser
385                 390                 395                 400

Val Asn Ala Thr Arg Gly Met Ile Val Asp Leu Lys Ala Thr Asp Pro
                405                 410                 415

Ala Gly Trp Gln Gly Asp His Glu Gln Thr Pro Ala Asn Pro Val Asp
            420                 425                 430

Glu Val Ile Tyr Glu Ala His Val Arg Asp Phe Ser Ile Asp Ala Asn
                435                 440                 445

Ser Gly Met Lys Asn Lys Gly Lys Tyr Leu Ala Phe Thr Glu His Gly
            450                 455                 460

Thr Lys Gly Pro Asp His Val Lys Thr Gly Ile Asp Ser Leu Lys Glu
465                 470                 475                 480

Leu Gly Ile Thr Thr Val Gln Leu Gln Pro Val Glu Glu Phe Asn Ser
                485                 490                 495

Ile Asp Glu Thr Gln Pro Asp Thr Tyr Asn Trp Gly Tyr Asp Pro Arg
            500                 505                 510

Asn Tyr Asn Val Pro Glu Gly Ala Tyr Ala Thr Thr Pro Glu Gly Thr
        515                 520                 525

Ala Arg Ile Thr Glu Leu Lys Gln Leu Ile Gln Ser Leu His Gln Gln
        530                 535                 540

Arg Ile Gly Val Asn Met Asp Val Val Tyr Asn His Thr Phe Asp Val
545                 550                 555                 560

Met Val Ser Asp Phe Asp Lys Ile Val Pro Gln Tyr Tyr Arg Thr
                565                 570                 575

Asp Ser Asn Gly Asn Tyr Thr Asn Gly Ser Gly Cys Gly Asn Glu Phe
            580                 585                 590

Ala Thr Glu His Pro Met Ala Gln Lys Phe Val Leu Asp Ser Val Asn
        595                 600                 605

Tyr Trp Val Asn Glu Tyr His Val Asp Gly Phe Arg Phe Asp Leu Met
610                 615                 620

Ala Leu Leu Gly Lys Asp Thr Met Ala Lys Ile Ser Asn Glu Leu His
625                 630                 635                 640

Ala Ile Asn Pro Gly Ile Val Leu Tyr Gly Glu Pro Trp Thr Gly Gly
                645                 650                 655

Thr Ser Gly Leu Ser Ser Asp Gln Leu Val Thr Lys Gly Gln Gln Lys
            660                 665                 670
```

```
Gly Leu Gly Ile Gly Val Phe Asn Asp Asn Ile Arg Asn Gly Leu Asp
            675                 680                 685

Gly Asn Val Phe Asp Lys Thr Ala Gln Gly Phe Ala Thr Gly Asp Pro
        690                 695                 700

Asn Gln Val Asp Val Ile Lys Asn Gly Val Ile Gly Ser Ile Gln Asp
705                 710                 715                 720

Phe Thr Ser Ala Pro Ser Glu Thr Ile Asn Tyr Val Thr Ser His Asp
                725                 730                 735

Asn Met Thr Leu Trp Asp Lys Ile Leu Ala Ser Asn Pro Ser Asp Thr
            740                 745                 750

Glu Ala Asp Arg Ile Lys Met Asp Glu Leu Ala His Ala Val Val Phe
        755                 760                 765

Thr Ser Gln Gly Val Pro Phe Met Gln Gly Gly Glu Glu Met Leu Arg
    770                 775                 780

Thr Lys Gly Gly Asn Asp Asn Ser Tyr Asn Ala Gly Asp Ser Val Asn
785                 790                 795                 800

Gln Phe Asp Trp Ser Arg Lys Ala Gln Phe Lys Asp Val Phe Asp Tyr
                805                 810                 815

Phe Ser Ser Met Ile His Leu Arg Asn Gln His Pro Ala Phe Arg Met
            820                 825                 830

Thr Thr Ala Asp Gln Ile Lys Gln Asn Leu Thr Phe Leu Glu Ser Pro
        835                 840                 845

Thr Asn Thr Val Ala Phe Glu Leu Lys Asn Tyr Ala Asn His Asp Thr
850                 855                 860

Trp Lys Asn Ile Ile Val Met Tyr Asn Pro Asn Lys Thr Ser Gln Thr
865                 870                 875                 880

Leu Asn Leu Pro Ser Gly Asp Trp Thr Ile Val Gly Leu Gly Asp Gln
                885                 890                 895

Ile Gly Glu Lys Ser Leu Gly His Val Met Gly Asn Val Gln Val Pro
            900                 905                 910

Ala Ile Ser Thr Leu Ile Leu Lys Gln
        915                 920

<210> SEQ ID NO 3
<211> LENGTH: 2787
<212> TYPE: DNA
<213> ORGANISM: Bacillus deramificans
<220> FEATURE:
<221> NAME/KEY: CDS
<222> LOCATION: (1)...(2784)

<400> SEQUENCE: 3 gat ggg aac acg aca acg atc att gtc cac tat ttt cgc cct gct ggt     48
Asp Gly Asn Thr Thr Thr Ile Ile Val His Tyr Phe Arg Pro Ala Gly
1               5                   10                  15 gat tat caa cct tgg agt cta tgg atg tgg cca aaa gac gga ggt ggg     96
Asp Tyr Gln Pro Trp Ser Leu Trp Met Trp Pro Lys Asp Gly Gly Gly
            20                  25                  30 gct gaa tac gat ttc aat caa ccg gct gac tct ttt gga gct gtt gca    144
Ala Glu Tyr Asp Phe Asn Gln Pro Ala Asp Ser Phe Gly Ala Val Ala
        35                  40                  45 agt gct gat att cca gga aac cca agt cag gta gga att atc gtt cgc    192
Ser Ala Asp Ile Pro Gly Asn Pro Ser Gln Val Gly Ile Ile Val Arg
    50                  55                  60 act caa gat tgg acc aaa gat gtg agc gct gac cgc tac ata gat tta    240
Thr Gln Asp Trp Thr Lys Asp Val Ser Ala Asp Arg Tyr Ile Asp Leu
65                  70                  75                  80
```

-continued

| | |
|---|---|
| agc aaa gga aat gag gtg tgg ctt gta gaa gga aac agc caa att ttt<br>Ser Lys Gly Asn Glu Val Trp Leu Val Glu Gly Asn Ser Gln Ile Phe<br>                85                    90                    95 | 288 |
| tat aat gaa aaa gat gct gag gat gca gct aaa ccc gct gta agc aac<br>Tyr Asn Glu Lys Asp Ala Glu Asp Ala Ala Lys Pro Ala Val Ser Asn<br>            100                 105                110 | 336 |
| gct tat tta gat gct tca aac cag gtg ctg gtt aaa ctt agc cag ccg<br>Ala Tyr Leu Asp Ala Ser Asn Gln Val Leu Val Lys Leu Ser Gln Pro<br>         115                120                125 | 384 |
| tta act ctt ggg gaa ggc gca agc ggc ttt acg gtt cat gac gac aca<br>Leu Thr Leu Gly Glu Gly Ala Ser Gly Phe Thr Val His Asp Asp Thr<br>130                  135                140 | 432 |
| gca aat aag gat att cca gtg aca tct gtg aag gat gca agt ctt ggt<br>Ala Asn Lys Asp Ile Pro Val Thr Ser Val Lys Asp Ala Ser Leu Gly<br>145                 150              155              160 | 480 |
| caa gat gta acc gct gtt ttg gca ggt acc ttc caa cat att ttt gga<br>Gln Asp Val Thr Ala Val Leu Ala Gly Thr Phe Gln His Ile Phe Gly<br>               165              170              175 | 528 |
| ggt tcc gat tgg gca cct gat aat cac agt act tta tta aaa aag gtg<br>Gly Ser Asp Trp Ala Pro Asp Asn His Ser Thr Leu Leu Lys Lys Val<br>         180                185                190 | 576 |
| act aac aat ctc tat caa ttc tca gga gat ctt cct gaa gga aac tac<br>Thr Asn Asn Leu Tyr Gln Phe Ser Gly Asp Leu Pro Glu Gly Asn Tyr<br>             195              200              205 | 624 |
| caa tat aaa gtg gct tta aat gat agc tgg aat aat ccg agt tac cca<br>Gln Tyr Lys Val Ala Leu Asn Asp Ser Trp Asn Asn Pro Ser Tyr Pro<br>210                 215              220 | 672 |
| tct gac aac att aat tta aca gtc cct gcc ggc ggt gca cac gtc act<br>Ser Asp Asn Ile Asn Leu Thr Val Pro Ala Gly Gly Ala His Val Thr<br>225                 230              235              240 | 720 |
| ttt tcg tat att ccg tcc act cat gca gtc tat gac aca att aat aat<br>Phe Ser Tyr Ile Pro Ser Thr His Ala Val Tyr Asp Thr Ile Asn Asn<br>               245              250              255 | 768 |
| cct aat gcg gat tta caa gta gaa agc ggg gtt aaa acg gat ctc gtg<br>Pro Asn Ala Asp Leu Gln Val Glu Ser Gly Val Lys Thr Asp Leu Val<br>         260                265                270 | 816 |
| acg gtt act cta ggg gaa gat cca gat gtg agc cat act ctg tcc att<br>Thr Val Thr Leu Gly Glu Asp Pro Asp Val Ser His Thr Leu Ser Ile<br>         275                280                285 | 864 |
| caa aca gat ggc tat cag gca aag cag gtg ata cct cgt aat gtg ctt<br>Gln Thr Asp Gly Tyr Gln Ala Lys Gln Val Ile Pro Arg Asn Val Leu<br>290                 295              300 | 912 |
| aat tca tca cag tac tac tat tca gga gat gat ctt ggg aat acc tat<br>Asn Ser Ser Gln Tyr Tyr Tyr Ser Gly Asp Asp Leu Gly Asn Thr Tyr<br>305                 310              315              320 | 960 |
| aca cag aaa gca aca acc ttt aaa gtc tgg gca cca act tct act caa<br>Thr Gln Lys Ala Thr Thr Phe Lys Val Trp Ala Pro Thr Ser Thr Gln<br>             325              330              335 | 1008 |
| gta aat gtt ctt ctt tat gac agt gca acg ggt tct gta aca aaa atc<br>Val Asn Val Leu Leu Tyr Asp Ser Ala Thr Gly Ser Val Thr Lys Ile<br>         340                345                350 | 1056 |
| gta cct atg acg gca tcg ggc cat ggt gtg tgg gaa gca acg gtt aat<br>Val Pro Met Thr Ala Ser Gly His Gly Val Trp Glu Ala Thr Val Asn<br>         355                360                365 | 1104 |
| caa aac ctt gaa aat tgg tat tac atg tat gag gta aca ggc caa ggc<br>Gln Asn Leu Glu Asn Trp Tyr Tyr Met Tyr Glu Val Thr Gly Gln Gly<br>         370                375                380 | 1152 |
| tct acc cga acg gct gtt gat cct tat gca act gcg att gca cca aat<br>Ser Thr Arg Thr Ala Val Asp Pro Tyr Ala Thr Ala Ile Ala Pro Asn<br>385                 390              395              400 | 1200 |

```
gga acg aga ggc atg att gtg gac ctg gct aaa aca gat cct gct ggc    1248
Gly Thr Arg Gly Met Ile Val Asp Leu Ala Lys Thr Asp Pro Ala Gly
            405                 410                 415 tgg aac agt gat aaa cat att acg cca aag aat ata gaa gat gag gtc    1296
Trp Asn Ser Asp Lys His Ile Thr Pro Lys Asn Ile Glu Asp Glu Val
        420                 425                 430 atc tat gaa atg gat gtc cgt gac ttt tcc att gac cct aat tcg ggt    1344
Ile Tyr Glu Met Asp Val Arg Asp Phe Ser Ile Asp Pro Asn Ser Gly
    435                 440                 445 atg aaa aat aaa ggg aag tat ttg gct ctt aca gaa aaa gga aca aag    1392
Met Lys Asn Lys Gly Lys Tyr Leu Ala Leu Thr Glu Lys Gly Thr Lys
450                 455                 460 ggc cct gac aac gta aag acg ggg ata gat tcc tta aaa caa ctt ggg    1440
Gly Pro Asp Asn Val Lys Thr Gly Ile Asp Ser Leu Lys Gln Leu Gly
465                 470                 475                 480 att act cat gtt cag ctt atg cct gtt ttc gca tct aac agt gtc gat    1488
Ile Thr His Val Gln Leu Met Pro Val Phe Ala Ser Asn Ser Val Asp
                485                 490                 495 gaa act gat cca acc caa gat aat tgg ggt tat gac cct cgc aac tat    1536
Glu Thr Asp Pro Thr Gln Asp Asn Trp Gly Tyr Asp Pro Arg Asn Tyr
            500                 505                 510 gat gtt cct gaa ggg cag tat gct aca aat gcg aat ggt aat gct cgt    1584
Asp Val Pro Glu Gly Gln Tyr Ala Thr Asn Ala Asn Gly Asn Ala Arg
        515                 520                 525 ata aaa gag ttt aag gaa atg gtt ctt tca ctc cat cgt gaa cac att    1632
Ile Lys Glu Phe Lys Glu Met Val Leu Ser Leu His Arg Glu His Ile
    530                 535                 540 ggg gtt aac atg gat gtt gtc tat aat cat acc ttt gcc acg caa atc    1680
Gly Val Asn Met Asp Val Val Tyr Asn His Thr Phe Ala Thr Gln Ile
545                 550                 555                 560 tct gac ttc gat aaa att gta cca gaa tat tat tac cgt acg gat gat    1728
Ser Asp Phe Asp Lys Ile Val Pro Glu Tyr Tyr Tyr Arg Thr Asp Asp
                565                 570                 575 gca ggt aat tat acc aac gga tca ggt act gga aat gaa att gca gcc    1776
Ala Gly Asn Tyr Thr Asn Gly Ser Gly Thr Gly Asn Glu Ile Ala Ala
            580                 585                 590 gaa agg cca atg gtt caa aaa ttt att att gat tcc ctt aag tat tgg    1824
Glu Arg Pro Met Val Gln Lys Phe Ile Ile Asp Ser Leu Lys Tyr Trp
        595                 600                 605 gtc aat gag tat cat att gac ggc ttc cgt ttt gac tta atg gcg ctg    1872
Val Asn Glu Tyr His Ile Asp Gly Phe Arg Phe Asp Leu Met Ala Leu
    610                 615                 620 ctt gga aaa gac acg atg tcc aaa gct gcc tcg gag ctt cat gct att    1920
Leu Gly Lys Asp Thr Met Ser Lys Ala Ala Ser Glu Leu His Ala Ile
625                 630                 635                 640 aat cca gga att gca ctt tac ggt gag cca tgg acg ggt gga acc tct    1968
Asn Pro Gly Ile Ala Leu Tyr Gly Glu Pro Trp Thr Gly Gly Thr Ser
                645                 650                 655 gca ctg cca gat gat cag ctt ctg aca aaa gga gct caa aaa ggc atg    2016
Ala Leu Pro Asp Asp Gln Leu Leu Thr Lys Gly Ala Gln Lys Gly Met
            660                 665                 670 gga gta gcg gtg ttt aat gac aat tta cga aac gcg ttg gac ggc aat    2064
Gly Val Ala Val Phe Asn Asp Asn Leu Arg Asn Ala Leu Asp Gly Asn
        675                 680                 685 gtc ttt gat tct tcc gct caa ggt ttt gcg aca ggt gca aca ggc tta    2112
Val Phe Asp Ser Ser Ala Gln Gly Phe Ala Thr Gly Ala Thr Gly Leu
    690                 695                 700 act gat gca att aag aat ggc gtt gag ggg agt att aat gac ttt acc    2160
Thr Asp Ala Ile Lys Asn Gly Val Glu Gly Ser Ile Asn Asp Phe Thr
```

```
                705                 710                 715                 720
tct tca cca ggt gag aca att aac tat gtc aca agt cat gat aac tac        2208
Ser Ser Pro Gly Glu Thr Ile Asn Tyr Val Thr Ser His Asp Asn Tyr
                    725                 730                 735 acc ctt tgg gac aaa ata gcc cta agc aat cct aat gat tcc gaa gcg        2256
Thr Leu Trp Asp Lys Ile Ala Leu Ser Asn Pro Asn Asp Ser Glu Ala
                740                 745                 750 gat cgg att aaa atg gat gaa ctc gca caa gca gtt gtt atg acc tca        2304
Asp Arg Ile Lys Met Asp Glu Leu Ala Gln Ala Val Val Met Thr Ser
            755                 760                 765 caa ggc gtt cca ttc atg caa ggc ggg gaa gaa atg ctt cgt aca aaa        2352
Gln Gly Val Pro Phe Met Gln Gly Gly Glu Glu Met Leu Arg Thr Lys
        770                 775                 780 ggc ggc aac gac aat agt tat aat gca ggc gat gcg gtc aat gag ttt        2400
Gly Gly Asn Asp Asn Ser Tyr Asn Ala Gly Asp Ala Val Asn Glu Phe
785                 790                 795                 800 gat tgg agc agg aaa gct caa tat cca gat gtt ttc aac tat tat agc        2448
Asp Trp Ser Arg Lys Ala Gln Tyr Pro Asp Val Phe Asn Tyr Tyr Ser
                    805                 810                 815 ggg cta atc cac ctt cgt ctt gat cac cca gcc ttc cgc atg acg aca        2496
Gly Leu Ile His Leu Arg Leu Asp His Pro Ala Phe Arg Met Thr Thr
                820                 825                 830 gct aat gaa atc aat agc cac ctc caa ttc cta aat agt cca gag aac        2544
Ala Asn Glu Ile Asn Ser His Leu Gln Phe Leu Asn Ser Pro Glu Asn
            835                 840                 845 aca gtg gcc tat gaa tta act gat cat gtt aat aaa gac aaa tgg gga        2592
Thr Val Ala Tyr Glu Leu Thr Asp His Val Asn Lys Asp Lys Trp Gly
        850                 855                 860 aat atc att gtt gtt tat aac cca aat aaa act gta gca acc atc aat        2640
Asn Ile Ile Val Val Tyr Asn Pro Asn Lys Thr Val Ala Thr Ile Asn
865                 870                 875                 880 ttg ccg agc ggg aaa tgg gca atc aat gct acg agc ggt aag gta gga        2688
Leu Pro Ser Gly Lys Trp Ala Ile Asn Ala Thr Ser Gly Lys Val Gly
                    885                 890                 895 gaa tcc acc ctt ggt caa gca gag gga agt gtc caa gta cca ggt ata        2736
Glu Ser Thr Leu Gly Gln Ala Glu Gly Ser Val Gln Val Pro Gly Ile
                900                 905                 910 tct atg atg atc ctt cat caa gag gta agc cca gac cac ggt aaa aag        2784
Ser Met Met Ile Leu His Gln Glu Val Ser Pro Asp His Gly Lys Lys
            915                 920                 925 taa                                                                    2787

<210> SEQ ID NO 4
<211> LENGTH: 928
<212> TYPE: PRT
<213> ORGANISM: Bacillus deramificans

<400> SEQUENCE: 4

Asp Gly Asn Thr Thr Ile Ile Val His Tyr Phe Arg Pro Ala Gly
 1               5                  10                  15

Asp Tyr Gln Pro Trp Ser Leu Trp Met Trp Pro Lys Asp Gly Gly
                20                  25                  30

Ala Glu Tyr Asp Phe Asn Gln Pro Ala Asp Ser Phe Gly Ala Val Ala
            35                  40                  45

Ser Ala Asp Ile Pro Gly Asn Pro Ser Gln Val Gly Ile Ile Val Arg
        50                  55                  60

Thr Gln Asp Trp Thr Lys Asp Val Ser Ala Asp Arg Tyr Ile Asp Leu
65                  70                  75                  80
```

```
Ser Lys Gly Asn Glu Val Trp Leu Val Glu Gly Asn Ser Gln Ile Phe
            85                  90                  95

Tyr Asn Glu Lys Asp Ala Glu Asp Ala Ala Lys Pro Ala Val Ser Asn
            100                 105                 110

Ala Tyr Leu Asp Ala Ser Asn Gln Val Leu Val Lys Leu Ser Gln Pro
            115                 120                 125

Leu Thr Leu Gly Glu Gly Ala Ser Gly Phe Thr Val His Asp Asp Thr
    130                 135                 140

Ala Asn Lys Asp Ile Pro Val Thr Ser Val Lys Asp Ala Ser Leu Gly
145                 150                 155                 160

Gln Asp Val Thr Ala Val Leu Ala Gly Thr Phe Gln His Ile Phe Gly
                165                 170                 175

Gly Ser Asp Trp Ala Pro Asp Asn His Ser Thr Leu Leu Lys Lys Val
            180                 185                 190

Thr Asn Asn Leu Tyr Gln Phe Ser Gly Asp Leu Pro Glu Gly Asn Tyr
            195                 200                 205

Gln Tyr Lys Val Ala Leu Asn Asp Ser Trp Asn Asn Pro Ser Tyr Pro
    210                 215                 220

Ser Asp Asn Ile Asn Leu Thr Val Pro Ala Gly Gly Ala His Val Thr
225                 230                 235                 240

Phe Ser Tyr Ile Pro Ser Thr His Ala Val Tyr Asp Thr Ile Asn Asn
                245                 250                 255

Pro Asn Ala Asp Leu Gln Val Glu Ser Gly Val Lys Thr Asp Leu Val
            260                 265                 270

Thr Val Thr Leu Gly Glu Asp Pro Asp Val Ser His Thr Leu Ser Ile
            275                 280                 285

Gln Thr Asp Gly Tyr Gln Ala Lys Gln Val Ile Pro Arg Asn Val Leu
    290                 295                 300

Asn Ser Ser Gln Tyr Tyr Tyr Ser Gly Asp Asp Leu Gly Asn Thr Tyr
305                 310                 315                 320

Thr Gln Lys Ala Thr Thr Phe Lys Val Trp Ala Pro Thr Ser Thr Gln
                325                 330                 335

Val Asn Val Leu Leu Tyr Asp Ser Ala Thr Gly Ser Val Thr Lys Ile
            340                 345                 350

Val Pro Met Thr Ala Ser Gly His Gly Val Trp Glu Ala Thr Val Asn
            355                 360                 365

Gln Asn Leu Glu Asn Trp Tyr Tyr Met Tyr Glu Val Thr Gly Gln Gly
    370                 375                 380

Ser Thr Arg Thr Ala Val Asp Pro Tyr Ala Thr Ala Ile Ala Pro Asn
385                 390                 395                 400

Gly Thr Arg Gly Met Ile Val Asp Leu Ala Lys Thr Asp Pro Ala Gly
                405                 410                 415

Trp Asn Ser Asp Lys His Ile Thr Pro Lys Asn Ile Glu Asp Glu Val
            420                 425                 430

Ile Tyr Glu Met Asp Val Arg Asp Phe Ser Ile Asp Pro Asn Ser Gly
    435                 440                 445

Met Lys Asn Lys Gly Lys Tyr Leu Ala Leu Thr Glu Lys Gly Thr Lys
    450                 455                 460

Gly Pro Asp Asn Val Lys Thr Gly Ile Asp Ser Leu Lys Gln Leu Gly
465                 470                 475                 480
```

```
Ile Thr His Val Gln Leu Met Pro Val Phe Ala Ser Asn Ser Val Asp
            485                 490                 495

Glu Thr Asp Pro Thr Gln Asp Asn Trp Gly Tyr Asp Pro Arg Asn Tyr
            500                 505                 510

Asp Val Pro Glu Gly Gln Tyr Ala Thr Asn Ala Asn Gly Asn Ala Arg
            515                 520                 525

Ile Lys Glu Phe Lys Glu Met Val Leu Ser Leu His Arg Glu His Ile
            530                 535                 540

Gly Val Asn Met Asp Val Val Tyr Asn His Thr Phe Ala Thr Gln Ile
545                 550                 555                 560

Ser Asp Phe Asp Lys Ile Val Pro Glu Tyr Tyr Arg Thr Asp Asp
            565                 570                 575

Ala Gly Asn Tyr Thr Asn Gly Ser Gly Thr Gly Asn Glu Ile Ala Ala
            580                 585                 590

Glu Arg Pro Met Val Gln Lys Phe Ile Ile Asp Ser Leu Lys Tyr Trp
            595                 600                 605

Val Asn Glu Tyr His Ile Asp Gly Phe Arg Phe Asp Leu Met Ala Leu
            610                 615                 620

Leu Gly Lys Asp Thr Met Ser Lys Ala Ala Ser Glu Leu His Ala Ile
625                 630                 635                 640

Asn Pro Gly Ile Ala Leu Tyr Gly Glu Pro Trp Thr Gly Gly Thr Ser
            645                 650                 655

Ala Leu Pro Asp Asp Gln Leu Leu Thr Lys Gly Ala Gln Lys Gly Met
            660                 665                 670

Gly Val Ala Val Phe Asn Asp Asn Leu Arg Asn Ala Leu Asp Gly Asn
            675                 680                 685

Val Phe Asp Ser Ser Ala Gln Gly Phe Ala Thr Gly Ala Thr Gly Leu
            690                 695                 700

Thr Asp Ala Ile Lys Asn Gly Val Glu Gly Ser Ile Asn Asp Phe Thr
705                 710                 715                 720

Ser Ser Pro Gly Glu Thr Ile Asn Tyr Val Thr Ser His Asp Asn Tyr
            725                 730                 735

Thr Leu Trp Asp Lys Ile Ala Leu Ser Asn Pro Asn Asp Ser Glu Ala
            740                 745                 750

Asp Arg Ile Lys Met Asp Glu Leu Ala Gln Ala Val Val Met Thr Ser
            755                 760                 765

Gln Gly Val Pro Phe Met Gln Gly Gly Glu Glu Met Leu Arg Thr Lys
            770                 775                 780

Gly Gly Asn Asp Asn Ser Tyr Asn Ala Gly Asp Ala Val Asn Glu Phe
785                 790                 795                 800

Asp Trp Ser Arg Lys Ala Gln Tyr Pro Asp Val Phe Asn Tyr Tyr Ser
            805                 810                 815

Gly Leu Ile His Leu Arg Leu Asp His Pro Ala Phe Arg Met Thr Thr
            820                 825                 830

Ala Asn Glu Ile Asn Ser His Leu Gln Phe Leu Asn Ser Pro Glu Asn
            835                 840                 845

Thr Val Ala Tyr Glu Leu Thr Asp His Val Asn Lys Asp Lys Trp Gly
            850                 855                 860

Asn Ile Ile Val Val Tyr Asn Pro Asn Lys Thr Val Ala Thr Ile Asn
865                 870                 875                 880
```

-continued

```
Leu Pro Ser Gly Lys Trp Ala Ile Asn Ala Thr Ser Gly Lys Val Gly
                885                 890                 895

Glu Ser Thr Leu Gly Gln Ala Glu Gly Ser Val Gln Val Pro Gly Ile
            900                 905                 910

Ser Met Met Ile Leu His Gln Glu Val Ser Pro Asp His Gly Lys Lys
        915                 920                 925

<210> SEQ ID NO 5
<211> LENGTH: 2487
<212> TYPE: DNA
<213> ORGANISM: Bacillius acidopullulyticus
<220> FEATURE:
<221> NAME/KEY: CDS
<222> LOCATION: (1)...(2487)

<400> SEQUENCE: 5 gat tct acc tcg aca gaa gtc att gtg cat tat cat cgt ttt gat tct       48
Asp Ser Thr Ser Thr Glu Val Ile Val His Tyr His Arg Phe Asp Ser
 1               5                  10                  15 aac tat gca aat tgg gat cta tgg atg tgg cca tat caa cca gtt aat       96
Asn Tyr Ala Asn Trp Asp Leu Trp Met Trp Pro Tyr Gln Pro Val Asn
             20                  25                  30 ggt aat gga gca gca tac gag ttt tct gga aag gat gat ttt ggc gtt      144
Gly Asn Gly Ala Ala Tyr Glu Phe Ser Gly Lys Asp Asp Phe Gly Val
         35                  40                  45 aaa gca gat gtt caa gtg cct ggg gat gat aca cag gta ggt ctg att      192
Lys Ala Asp Val Gln Val Pro Gly Asp Asp Thr Gln Val Gly Leu Ile
     50                  55                  60 gtc cgt aca aat gat tgg agc caa aaa aat aca tca gac gat ctc cat      240
Val Arg Thr Asn Asp Trp Ser Gln Lys Asn Thr Ser Asp Asp Leu His
 65                  70                  75                  80 att gat ctg aca aag ggg cat gaa ata tgg att gtt cag ggg gat ccc      288
Ile Asp Leu Thr Lys Gly His Glu Ile Trp Ile Val Gln Gly Asp Pro
                 85                  90                  95 aat att tat tac aat ctg agt gat gcg cag gct gca gcg act cca aag      336
Asn Ile Tyr Tyr Asn Leu Ser Asp Ala Gln Ala Ala Ala Thr Pro Lys
            100                 105                 110 gtt tcg aat gcg tat ttg gat aat gaa aaa aca gta ttg gca aag cta      384
Val Ser Asn Ala Tyr Leu Asp Asn Glu Lys Thr Val Leu Ala Lys Leu
        115                 120                 125 act aat cca atg aca tta tca gat gga tca agc ggc ttt acg gtt aca      432
Thr Asn Pro Met Thr Leu Ser Asp Gly Ser Ser Gly Phe Thr Val Thr
    130                 135                 140 gat aaa aca aca ggg gaa caa att cca gtt acc gct gca aca aat gcg      480
Asp Lys Thr Thr Gly Glu Gln Ile Pro Val Thr Ala Ala Thr Asn Ala
145                 150                 155                 160 aac tca gcc tcc tcg tct gag cag aca gac ttg gtt caa ttg acg tta      528
Asn Ser Ala Ser Ser Ser Glu Gln Thr Asp Leu Val Gln Leu Thr Leu
                165                 170                 175 gcc agt gca ccg gat gtt tcc cat aca ata caa gta gga gca gcc ggt      576
Ala Ser Ala Pro Asp Val Ser His Thr Ile Gln Val Gly Ala Ala Gly
            180                 185                 190 tat gaa gca gtc aat ctc ata cca cga aat gta tta aat ttg cct cgt      624
Tyr Glu Ala Val Asn Leu Ile Pro Arg Asn Val Leu Asn Leu Pro Arg
        195                 200                 205 tat tat tac agc gga aat gat tta ggt aac gtt tat tca aat aag gca      672
Tyr Tyr Tyr Ser Gly Asn Asp Leu Gly Asn Val Tyr Ser Asn Lys Ala
    210                 215                 220 acg gcc ttc cgt gta tgg gct cca act gct tcg gat gtc caa tta ctt      720
Thr Ala Phe Arg Val Trp Ala Pro Thr Ala Ser Asp Val Gln Leu Leu
225                 230                 235                 240
```

```
tta tac aat agt gaa aca gga cct gta acc aaa cag ctt gaa atg caa       768
Leu Tyr Asn Ser Glu Thr Gly Pro Val Thr Lys Gln Leu Glu Met Gln
                245                 250                 255 aag agt gat aac ggt aca tgg aaa ctg aag gtc cct ggt aat ctg aaa       816
Lys Ser Asp Asn Gly Thr Trp Lys Leu Lys Val Pro Gly Asn Leu Lys
            260                 265                 270 aat tgg tat tat ctc tat cag gta acg gtg aat ggg aag aca caa aca       864
Asn Trp Tyr Tyr Leu Tyr Gln Val Thr Val Asn Gly Lys Thr Gln Thr
        275                 280                 285 gcc gtt gac cct tat gtg cgt gct att tca gtc aat gca aca cgt ggt       912
Ala Val Asp Pro Tyr Val Arg Ala Ile Ser Val Asn Ala Thr Arg Gly
    290                 295                 300 atg ata gtc gat tta gaa gat acg aat cct cct gga tgg aaa gaa gat       960
Met Ile Val Asp Leu Glu Asp Thr Asn Pro Pro Gly Trp Lys Glu Asp
305                 310                 315                 320 cat caa cag aca cct gcg aac cca gtg gat gaa gta atc tac gaa gtg      1008
His Gln Gln Thr Pro Ala Asn Pro Val Asp Glu Val Ile Tyr Glu Val
                325                 330                 335 cat gtg cgt gat ttt tcg att gat gct aat tca ggc atg aaa aat aaa      1056
His Val Arg Asp Phe Ser Ile Asp Ala Asn Ser Gly Met Lys Asn Lys
            340                 345                 350 ggg aaa tat ctt gcc ttt aca gaa cat ggc aca aaa ggc cct gat aac      1104
Gly Lys Tyr Leu Ala Phe Thr Glu His Gly Thr Lys Gly Pro Asp Asn
        355                 360                 365 gtg aaa acg ggt att gat agt ttg aag gaa tta gga atc aat gct gtt      1152
Val Lys Thr Gly Ile Asp Ser Leu Lys Glu Leu Gly Ile Asn Ala Val
    370                 375                 380 caa tta cag ccg att gaa gaa ttt aac agc att gat gaa acc caa cca      1200
Gln Leu Gln Pro Ile Glu Glu Phe Asn Ser Ile Asp Glu Thr Gln Pro
385                 390                 395                 400 aat atg tat aac tgg ggc tat gac cca aga aac tac aac gtc cct gaa      1248
Asn Met Tyr Asn Trp Gly Tyr Asp Pro Arg Asn Tyr Asn Val Pro Glu
                405                 410                 415 gga gcg tat gca act aca cca gaa gga acg gct cgc att acc cag tta      1296
Gly Ala Tyr Ala Thr Thr Pro Glu Gly Thr Ala Arg Ile Thr Gln Leu
            420                 425                 430 aag caa ctg att caa agc att cat aaa gat cgg att gct atc aat atg      1344
Lys Gln Leu Ile Gln Ser Ile His Lys Asp Arg Ile Ala Ile Asn Met
        435                 440                 445 gat gtg gtc tat aac cat acc ttt aac gta gga gtg tct gat ttt gat      1392
Asp Val Val Tyr Asn His Thr Phe Asn Val Gly Val Ser Asp Phe Asp
    450                 455                 460 aag att gtt ccg caa tac tat tat cgg aca gac agc gca ggt aat tat      1440
Lys Ile Val Pro Gln Tyr Tyr Tyr Arg Thr Asp Ser Ala Gly Asn Tyr
465                 470                 475                 480 acg aac ggc tca ggt gta ggt aat gaa att gcg acc gag cgt ccg atg      1488
Thr Asn Gly Ser Gly Val Gly Asn Glu Ile Ala Thr Glu Arg Pro Met
                485                 490                 495 gtc caa aag ttc gtt ctg gat tct gtt aaa tat tgg gta aag gaa tac      1536
Val Gln Lys Phe Val Leu Asp Ser Val Lys Tyr Trp Val Lys Glu Tyr
            500                 505                 510 cat atc gac ggc ttc cgt ttc gat ctt atg gct ctt tta gga aaa gac      1584
His Ile Asp Gly Phe Arg Phe Asp Leu Met Ala Leu Leu Gly Lys Asp
        515                 520                 525 acc atg gcc aaa ata tca aaa gag ctt cat gct att aat cct ggc att      1632
Thr Met Ala Lys Ile Ser Lys Glu Leu His Ala Ile Asn Pro Gly Ile
530                 535                 540 gtc ctg tat gga gaa cca tgg act ggc ggt acc tct gga tta tca agc      1680
Val Leu Tyr Gly Glu Pro Trp Thr Gly Gly Thr Ser Gly Leu Ser Ser
```

-continued

| | | |
|---|---|---|
| gac caa ctc gtt acg aaa ggt cag caa aag ggc ttg gga att ggc gta<br>Asp Gln Leu Val Thr Lys Gly Gln Gln Lys Gly Leu Gly Ile Gly Val<br>545              550                555                560 | 1728 |
| ttc aac gat aat att cgg aac gga ctc gat ggt aac gtt ttt gat aaa<br>Phe Asn Asp Asn Ile Arg Asn Gly Leu Asp Gly Asn Val Phe Asp Lys<br>565              580                585                590 | 1776 |
| tcg gca caa gga ttt gca aca gga gat cca aac caa gtt aat gtc att<br>Ser Ala Gln Gly Phe Ala Thr Gly Asp Pro Asn Gln Val Asn Val Ile<br>595              600                605 | 1824 |
| aaa aat aga gtt atg gga agt att tca gat ttc act tcg gca cct agc<br>Lys Asn Arg Val Met Gly Ser Ile Ser Asp Phe Thr Ser Ala Pro Ser<br>610                615                620 | 1872 |
| gaa acc att aac tat gta aca agc cat gat aat atg aca ttg tgg gat<br>Glu Thr Ile Asn Tyr Val Thr Ser His Asp Asn Met Thr Leu Trp Asp<br>625              630                635                640 | 1920 |
| aaa att agc gca agt aat ccg aac gat aca caa gca gat cga att aag<br>Lys Ile Ser Ala Ser Asn Pro Asn Asp Thr Gln Ala Asp Arg Ile Lys<br>645              650                655 | 1968 |
| atg gat gaa ttg gct caa gct gtg gta ttt act tca caa ggg gta cca<br>Met Asp Glu Leu Ala Gln Ala Val Val Phe Thr Ser Gln Gly Val Pro<br>660              665                670 | 2016 |
| ttt atg caa ggt gga gaa gaa atg ctg cgg aca aaa ggc ggt aat gat<br>Phe Met Gln Gly Gly Glu Glu Met Leu Arg Thr Lys Gly Gly Asn Asp<br>675              680                685 | 2064 |
| aat agt tac aat gcc ggg gat agc gtg aat cag ttc gat tgg tca aga<br>Asn Ser Tyr Asn Ala Gly Asp Ser Val Asn Gln Phe Asp Trp Ser Arg<br>690              695                700 | 2112 |
| aaa gca caa ttt gaa aat gta ttc gac tac tat tct tgg ttg att cat<br>Lys Ala Gln Phe Glu Asn Val Phe Asp Tyr Tyr Ser Trp Leu Ile His<br>705              710                715                720 | 2160 |
| cta cgt gat aat cac cca gca ttc cgt atg acg aca gcg gat caa atc<br>Leu Arg Asp Asn His Pro Ala Phe Arg Met Thr Thr Ala Asp Gln Ile<br>725              730                735 | 2208 |
| aaa caa aat ctc act ttc ttg gat agc cca acg aac act gta gca ttt<br>Lys Gln Asn Leu Thr Phe Leu Asp Ser Pro Thr Asn Thr Val Ala Phe<br>740              745                750 | 2256 |
| gaa tta aaa aat cat gcc aat cat gat aaa tgg aaa aac att ata gtt<br>Glu Leu Lys Asn His Ala Asn His Asp Lys Trp Lys Asn Ile Ile Val<br>755              760                765 | 2304 |
| atg tat aat cca aat aaa act gca caa act ctc act cta cca agt gga<br>Met Tyr Asn Pro Asn Lys Thr Ala Gln Thr Leu Thr Leu Pro Ser Gly<br>770              775                780 | 2352 |
| aat tgg aca att gta gga tta ggc aat caa gta ggt gag aaa tca cta<br>Asn Trp Thr Ile Val Gly Leu Gly Asn Gln Val Gly Glu Lys Ser Leu<br>785              790                795                800 | 2400 |
| ggc cat gta aat ggc acg gtt gag gtg cca gct ctt agt acg atc att<br>Gly His Val Asn Gly Thr Val Glu Val Pro Ala Leu Ser Thr Ile Ile<br>805              810                815 | 2448 |
| ctt cat cag ggt aca tct gaa gat gtc att gat caa aat<br>Leu His Gln Gly Thr Ser Glu Asp Val Ile Asp Gln Asn<br>820              825 | 2487 |

<210> SEQ ID NO 6
<211> LENGTH: 829
<212> TYPE: PRT
<213> ORGANISM: Bacillius acidopullulyticus

<400> SEQUENCE: 6

```
Asp Ser Thr Ser Thr Glu Val Ile Val His Tyr His Arg Phe Asp Ser
 1               5                  10                  15

Asn Tyr Ala Asn Trp Asp Leu Trp Met Trp Pro Tyr Gln Pro Val Asn
            20                  25                  30

Gly Asn Gly Ala Ala Tyr Glu Phe Ser Gly Lys Asp Asp Phe Gly Val
        35                  40                  45

Lys Ala Asp Val Gln Val Pro Gly Asp Thr Gln Val Gly Leu Ile
50                  55                  60

Val Arg Thr Asn Asp Trp Ser Gln Lys Asn Thr Ser Asp Asp Leu His
65                  70                  75                  80

Ile Asp Leu Thr Lys Gly His Glu Ile Trp Ile Val Gln Gly Asp Pro
                85                  90                  95

Asn Ile Tyr Tyr Asn Leu Ser Asp Ala Gln Ala Ala Thr Pro Lys
            100                 105                 110

Val Ser Asn Ala Tyr Leu Asp Asn Glu Lys Thr Val Leu Ala Lys Leu
            115                 120                 125

Thr Asn Pro Met Thr Leu Ser Asp Gly Ser Ser Gly Phe Thr Val Thr
        130                 135                 140

Asp Lys Thr Thr Gly Glu Gln Ile Pro Val Thr Ala Ala Thr Asn Ala
145                 150                 155                 160

Asn Ser Ala Ser Ser Glu Gln Thr Asp Leu Val Gln Leu Thr Leu
                165                 170                 175

Ala Ser Ala Pro Asp Val Ser His Thr Ile Gln Val Gly Ala Ala Gly
            180                 185                 190

Tyr Glu Ala Val Asn Leu Ile Pro Arg Asn Val Leu Asn Leu Pro Arg
        195                 200                 205

Tyr Tyr Tyr Ser Gly Asn Asp Leu Gly Asn Val Tyr Ser Asn Lys Ala
        210                 215                 220

Thr Ala Phe Arg Val Trp Ala Pro Thr Ala Ser Asp Val Gln Leu Leu
225                 230                 235                 240

Leu Tyr Asn Ser Glu Thr Gly Pro Val Thr Lys Gln Leu Glu Met Gln
            245                 250                 255

Lys Ser Asp Asn Gly Thr Trp Lys Leu Lys Val Pro Gly Asn Leu Lys
            260                 265                 270

Asn Trp Tyr Tyr Leu Tyr Gln Val Thr Val Asn Gly Lys Thr Gln Thr
        275                 280                 285

Ala Val Asp Pro Tyr Val Arg Ala Ile Ser Val Asn Ala Thr Arg Gly
        290                 295                 300

Met Ile Val Asp Leu Glu Asp Thr Asn Pro Pro Gly Trp Lys Glu Asp
305                 310                 315                 320

His Gln Gln Thr Pro Ala Asn Pro Val Asp Glu Val Ile Tyr Glu Val
                325                 330                 335

His Val Arg Asp Phe Ser Ile Asp Ala Asn Ser Gly Met Lys Asn Lys
                340                 345                 350

Gly Lys Tyr Leu Ala Phe Thr Glu His Gly Thr Lys Gly Pro Asp Asn
        355                 360                 365

Val Lys Thr Gly Ile Asp Ser Leu Lys Glu Leu Gly Ile Asn Ala Val
        370                 375                 380

Gln Leu Gln Pro Ile Glu Glu Phe Asn Ser Ile Asp Glu Thr Gln Pro
385                 390                 395                 400
```

-continued

```
Asn Met Tyr Asn Trp Gly Tyr Asp Pro Arg Asn Tyr Asn Val Pro Glu
                405                 410                 415
Gly Ala Tyr Ala Thr Thr Pro Glu Gly Thr Ala Arg Ile Thr Gln Leu
            420                 425                 430
Lys Gln Leu Ile Gln Ser Ile His Lys Asp Arg Ile Ala Ile Asn Met
        435                 440                 445
Asp Val Val Tyr Asn His Thr Phe Asn Val Gly Val Ser Asp Phe Asp
    450                 455                 460
Lys Ile Val Pro Gln Tyr Tyr Arg Thr Asp Ser Ala Gly Asn Tyr
465                 470                 475                 480
Thr Asn Gly Ser Gly Val Gly Asn Glu Ile Ala Thr Glu Arg Pro Met
            485                 490                 495
Val Gln Lys Phe Val Leu Asp Ser Val Lys Tyr Trp Val Lys Glu Tyr
        500                 505                 510
His Ile Asp Gly Phe Arg Phe Asp Leu Met Ala Leu Leu Gly Lys Asp
    515                 520                 525
Thr Met Ala Lys Ile Ser Lys Glu Leu His Ala Ile Asn Pro Gly Ile
530                 535                 540
Val Leu Tyr Gly Glu Pro Trp Thr Gly Gly Thr Ser Gly Leu Ser Ser
545                 550                 555                 560
Asp Gln Leu Val Thr Lys Gly Gln Gln Lys Gly Leu Gly Ile Gly Val
            565                 570                 575

Phe Asn Asp Asn Ile Arg Asn Gly Leu Asp Gly Asn Val Phe Asp Lys
            580                 585                 590
Ser Ala Gln Gly Phe Ala Thr Gly Asp Pro Asn Gln Val Asn Val Ile
        595                 600                 605
Lys Asn Arg Val Met Gly Ser Ile Ser Asp Phe Thr Ser Ala Pro Ser
    610                 615                 620
Glu Thr Ile Asn Tyr Val Thr Ser His Asp Asn Met Thr Leu Trp Asp
625                 630                 635                 640
Lys Ile Ser Ala Ser Asn Pro Asn Asp Thr Gln Ala Asp Arg Ile Lys
            645                 650                 655
Met Asp Glu Leu Ala Gln Ala Val Val Phe Thr Ser Gln Gly Val Pro
        660                 665                 670
Phe Met Gln Gly Gly Glu Glu Met Leu Arg Thr Lys Gly Gly Asn Asp
    675                 680                 685
Asn Ser Tyr Asn Ala Gly Asp Ser Val Asn Gln Phe Asp Trp Ser Arg
690                 695                 700
Lys Ala Gln Phe Glu Asn Val Phe Asp Tyr Tyr Ser Trp Leu Ile His
705                 710                 715                 720
Leu Arg Asp Asn His Pro Ala Phe Arg Met Thr Thr Ala Asp Gln Ile
            725                 730                 735
Lys Gln Asn Leu Thr Phe Leu Asp Ser Pro Thr Asn Thr Val Ala Phe
        740                 745                 750
Glu Leu Lys Asn His Ala Asn His Asp Lys Trp Lys Asn Ile Ile Val
    755                 760                 765
Met Tyr Asn Pro Asn Lys Thr Ala Gln Thr Leu Thr Leu Pro Ser Gly
770                 775                 780
Asn Trp Thr Ile Val Gly Leu Gly Asn Gln Val Gly Glu Lys Ser Leu
785                 790                 795                 800
Gly His Val Asn Gly Thr Val Glu Val Pro Ala Leu Ser Thr Ile Ile
```

-continued

```
                     805                 810                 815
Leu His Gln Gly Thr Ser Glu Asp Val Ile Asp Gln Asn
                820                 825

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
cgcttcggaa tcattaggat tgc                                    23

<210> SEQ ID NO 8
<211> LENGTH: 27
<212> TYPE: DNA
<213> ORGANISM: Artificial Sequence
<220> FEATURE:
<223> OTHER INFORMATION: Primer

<400> SEQUENCE: 8
gcttccgttt tgccttaatg gcgctgc                                27

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
ggccaaggct ctacccgaac ggc                                    23

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gcactttacg gggcgccatg gacggg                                 26
```